US007267941B2

(12) United States Patent
Snell et al.

(10) Patent No.: US 7,267,941 B2
(45) Date of Patent: Sep. 11, 2007

(54) CYANOVIRIN VARIANT-POLYMER CONJUGATES

(75) Inventors: M. Elizabeth Snell, Ardmore, AL (US); Michael J. Roberts, Williamsburg, VA (US); Toshiyuki Mori, Germantown, MD (US); Barry R. O'Keefe, Frederick, MD (US); Michael R. Boyd, Mobile, AL (US)

(73) Assignees: The Government of the United States of America as represented by The Secretary of The Department of Health and Human Services, The National Institutes of Health, Washington, DC (US); Nektar Therapeutics AL, Huntsville, AL (US)

( * ) Notice: Subject to any disclaimer, the term of this patent is extended or adjusted under 35 U.S.C. 154(b) by 322 days.

(21) Appl. No.: 10/742,465

(22) Filed: Dec. 18, 2003

(65) Prior Publication Data

US 2004/0258706 A1  Dec. 23, 2004

Related U.S. Application Data

(60) Provisional application No. 60/461,731, filed on Apr. 9, 2003, provisional application No. 60/435,950, filed on Dec. 19, 2002.

(51) Int. Cl.
*C12Q 1/70* (2006.01)
*C12P 21/06* (2006.01)
*C12P 21/04* (2006.01)
*A61B 5/055* (2006.01)
*A61K 39/00* (2006.01)

(52) U.S. Cl. .................. 435/5; 435/68.1; 435/71.1; 424/9.34; 424/134.1

(58) Field of Classification Search .................. None
See application file for complete search history.

(56) References Cited

U.S. PATENT DOCUMENTS 5,766,897 A    6/1998  Braxton
2002/0127675 A1* 9/2002 Boyd .......................... 435/184

FOREIGN PATENT DOCUMENTS

WO    WO 02/077189 A2   10/2002
WO    WO 03/066078 A1    8/2003

OTHER PUBLICATIONS

French et al., What is Conservative Substitution, 1983, Journal of Molecular Evolution vol. 16, pp. 171-175.*
Sigma-Aldrich, www.sigmaaldrich.com, Product=Polyethylene glycol, 1997.*
Copy of International Search report from PCT/US03/40585 filed on Dec. 18, 2003.

Roberts, M.J. et al., "Chemistry for peptide and protein PEGylation", *Advanced Drug Delivery Reviews* 54(4):459-476, 2002.
Goodson, R. J. et al., "Site-Directed Pegylation of Recombinant Interleukin-2 at Its Glycosylation Site", *Bio/Technology* 8:343-346, 1990.
O'Keefe, B. et al., "Analysis of the Interaction Between the HIV-Inactivating Protein Cyanovirin-N and Soluble Forms of the Envelope Glycoproteins gp120 and gp41", *Molevular Pharmacology* 58(5):982-992.
Mori, T. et al., "Functional homologs of cyanovirin-N amenable to mass production in prokaryotic and eurokaryotic hosts", *Protein Expression and Purification*, 26(1):42-49, 2002.
Botos, I. et al., "Domain-swapped structure of a mutant of cyanovirin-N", *Biochemical and Biophysical Research Communications*, 294(1):184-190, 2002.
Botos, I. et al., "Structures of the Complexes of a Potent Anti-HIV Protein Cyanovirin-N and High Mannose Oligosaccharides", *The Journal of Biological Chemistry*, 277(37): 34336-34342, Sep. 13, 2002.
Shenoy, S. R. et al., "Selective Interactions of the Human Immunodeficiency Virus-Inactivating Protein Cyanovirin-N with High-Mannose Oligosaccharides on gp120 and Other Glycoproteins", *The Journal of Pharmacology and Experimental Therapeutics*, 197(2):704-710, 2001.
Han, Z.Z. et al., "Discovery of a Stable Dimeric Mutant of Cyanovirin-N (CV-N) froma T7 Phage-Displayed CV-N Mutant Library", *Biochemical and Biophysical Research Communications*, 292(4):1036-1043, Apr. 12, 2002.
Bewley, C.A., "Solution Structure of a Cyanovirin-N:Manα 1-2Manα Complex: Structural Basis for High-Affinity Carbohydrate-Mediated Binding to gp120", *Structure (Camb.)* 9(10):931-940, Oct. 2001.
Bewley, C.A. and Otero-Quintero, S., The Potent Anti-HIV Protein Cyanovirin-N Contains Two Novel Carbohydrate Binding Sites That Selectively Bind to $Man_8$ D1D3 and $Man_9$ with Nanomolar Affinity: Implications for Binding to the HIV Envelope Protein gp120, *Journal of Amer. Chem. Soc.* 123(17):3892-3902, May 2, 2001.
Bewley, C.A., "Rapid Validation of the Overall Structure of an Internal Domain-Swapped Mutant of the Anti-HIV Proten Cyanovirin-N using Residual Dipolar Couplings", *Journal of Amer. Chem. Soc.* 123(5):1014-1015, Feb. 7, 2001.
Gandhi, M.J. et al., "Properties of Cyanovirin-N (CV-N): Inactivation of HIV-1 by Sessile Cyanovirin-N (sCV-N)", *Advances in Transfusion Safety, Dev. Biol. Stand.* 102:141-148, 2000.
Bewley, C.A., et al., "Solution structure of cyanovirin-N, a potent HIV-inactivating protein", *Nature Structural Biology* 5(7):571-578, Jul. 1998.
Mori, T. et al., Analysis of Sequence Requirement for Biological Activity of Cyanovirin-N, a Potent HIV (Human Immunodeficiency Virus)-Inactivating Protein[1,2n], *Biochemical and Biophysical Research Communications* 238(1):218-222, Sep. 8, 1997.

(Continued)

Primary Examiner—Bruce R. Campell
Assistant Examiner—Sharon Hurt
(74) Attorney, Agent, or Firm—Susan T. Evans; Leeann Gorthey; Perkins Cole LLP

(57) ABSTRACT

The present invention provides variants of cyanovirin-N and water-soluble polymer conjugates thereof. The cyanovirin-N of the invention are particularly suited for site-selective covalent attachment of one or more water soluble polymers, to provide polymer conjugates of cyanovirin-N variants exhibiting antiviral activity.

45 Claims, 2 Drawing Sheets

OTHER PUBLICATIONS

Boyd, M.R. et al., "Discovery of Cyanovirin-N, a Novel Human Immunodeficiency Virus-Inactivating Protein That Binds Viral Surface Envelope Glycoprotein gp120: Potential Applications to Microbicide Development", *Antimicrobial Agents and Chemotherapy*, 41(7):1521-1530, Jul. 1997.

Chang, L.C. and Bewley, C. A., "Potent Inhibition of HIV-1 Fusion by Cyanovirin-N Requires Only a Single high Affinity Carbohydrate Binding Site: Characterization of Low Affinity Carbohydrate Binding Site Knockout Mutants", *J. Mol. Biol.*, 318:1-8, Apr. 19, 2002.

* cited by examiner

SEQUENCE LISTING

```
<160> NUMBER OF SEQ ID NOS: 13

<210> SEQ ID NO 1
<211> LENGTH: 101
<212> TYPE: PRT
<213> ORGANISM: Nostoc ellipsosporum

<400> SEQUENCE: 1

Leu Gly Lys Phe Ser Gln Thr Cys Tyr Asn Ser Ala Ile Gln Gly Ser
 1               5                  10                  15

Val Leu Thr Ser Thr Cys Glu Arg Thr Asn Gly Gly Tyr Asn Thr Ser
            20                  25                  30

Ser Ile Asp Leu Asn Ser Val Ile Glu Asn Val Asp Gly Ser Leu Lys
        35                  40                  45

Trp Gln Pro Ser Asn Phe Ile Glu Thr Cys Arg Asn Thr Gln Leu Ala
    50                  55                  60

Gly Ser Ser Glu Leu Ala Ala Glu Cys Lys Thr Arg Ala Gln Gln Phe
65                  70                  75                  80

Val Ser Thr Lys Ile Asn Leu Asp Asp His Ile Ala Asn Ile Asp Gly
```

```
                    85                  90                  95

Thr Leu Lys Tyr Glu
            100

<210> SEQ ID NO 2
<211> LENGTH: 101
<212> TYPE: PRT
<213> ORGANISM: Artificial Sequence
<220> FEATURE:
<223> OTHER INFORMATION: cyanovirin-N variant
<220> FEATURE:
<221> NAME/KEY: VARIANT
<222> LOCATION: 3, 74
<223> OTHER INFORMATION: Xaa = Lys or Arg
<220> FEATURE:
<221> NAME/KEY: VARIANT
<222> LOCATION: 48, 84, 99
<223> OTHER INFORMATION: Xaa = Lys, Cys, or Arg
<220> FEATURE:
<221> NAME/KEY: VARIANT
<222> LOCATION: 9-21, 29-40, 45-47, 49, 57, 59-72, 79-83, 85-91
<223> OTHER INFORMATION: May be Cys substituted

<400> SEQUENCE: 2

Leu Gly Xaa Phe Ser Gln Thr Cys Tyr Asn Ser Ala Ile Gln Gly Ser
  1               5                  10                  15

Val Leu Thr Ser Thr Cys Glu Arg Thr Asn Gly Gly Tyr Asn Thr Ser
             20                  25                  30

Ser Ile Asp Leu Asn Ser Val Ile Glu Asn Val Asp Gly Ser Leu Xaa
         35                  40                  45

Trp Gln Pro Ser Asn Phe Ile Glu Thr Cys Arg Asn Thr Gln Leu Ala
 50                  55                  60

Gly Ser Ser Glu Leu Ala Ala Glu Cys Xaa Thr Arg Ala Gln Gln Phe
 65                  70                  75                  80

Val Ser Thr Xaa Ile Asn Leu Asp Asp His Ile Ala Asn Ile Asp Gly
             85                  90                  95

Thr Leu Xaa Tyr Glu
            100

<210> SEQ ID NO 3
<211> LENGTH: 101
<212> TYPE: PRT
<213> ORGANISM: Artificial Sequence
<220> FEATURE:
<223> OTHER INFORMATION: cyanovirin-N variant
<220> FEATURE:
<221> NAME/KEY: VARIANT
<222> LOCATION: 9-21, 29-40, 45-49, 57, 59-72, 79-91, 96-101
<223> OTHER INFORMATION: May be Cys substituted

<400> SEQUENCE: 3

Leu Gly Lys Phe Ser Gln Thr Cys Tyr Asn Ser Ala Ile Gln Gly Ser
  1               5                  10                  15

Val Leu Thr Ser Thr Cys Glu Arg Thr Asn Gly Gly Tyr Asn Thr Ser
             20                  25                  30

Ser Ile Asp Leu Asn Ser Val Ile Glu Asn Val Asp Gly Ser Leu Lys
         35                  40                  45

Trp Gln Pro Ser Asn Phe Ile Glu Thr Cys Arg Asn Thr Gln Leu Ala
 50                  55                  60

Gly Ser Ser Glu Leu Ala Ala Glu Cys Lys Thr Arg Ala Gln Gln Phe
 65                  70                  75                  80

Val Ser Thr Lys Ile Asn Leu Asp Asp His Ile Ala Asn Ile Asp Gly
             85                  90                  95
```

Thr Leu Lys Tyr Glu
            100

<210> SEQ ID NO 4
<211> LENGTH: 101
<212> TYPE: PRT
<213> ORGANISM: Artificial Sequence
<220> FEATURE:
<223> OTHER INFORMATION: cyanovirin-N variant
<220> FEATURE:
<221> NAME/KEY: VARIANT
<222> LOCATION: 10-20, 31-39, 46-48, 60-71, 80-90, 97-100
<223> OTHER INFORMATION: May be Cys substituted

<400> SEQUENCE: 4

Leu Gly Lys Phe Ser Gln Thr Cys Tyr Asn Ser Ala Ile Gln Gly Ser
1 5 10 15

Val Leu Thr Ser Thr Cys Glu Arg Thr Asn Gly Gly Tyr Asn Thr Ser
20 25 30

Ser Ile Asp Leu Asn Ser Val Ile Glu Asn Val Asp Gly Ser Leu Lys
35 40 45

Trp Gln Pro Ser Asn Phe Ile Glu Thr Cys Arg Asn Thr Gln Leu Ala
50 55 60

Gly Ser Ser Glu Leu Ala Ala Glu Cys Lys Thr Arg Ala Gln Gln Phe
65 70 75 80

Val Ser Thr Lys Ile Asn Leu Asp Asp His Ile Ala Asn Ile Asp Gly
85 90 95

Thr Leu Lys Tyr Glu
100

<210> SEQ ID NO 5
<211> LENGTH: 101
<212> TYPE: PRT
<213> ORGANISM: Artificial Sequence
<220> FEATURE:
<223> OTHER INFORMATION: cyanovirin-N variant
<220> FEATURE:
<221> NAME/KEY: VARIANT
<222> LOCATION: 11, 16, 20, 32, 33, 38, 46, 66, 67, 82
<223> OTHER INFORMATION: Xaa = Ser or Cys
<220> FEATURE:
<221> NAME/KEY: VARIANT
<222> LOCATION: 14, 62
<223> OTHER INFORMATION: Xaa = Gln or Cys
<220> FEATURE:
<221> NAME/KEY: VARIANT
<222> LOCATION: 19, 31, 61, 83
<223> OTHER INFORMATION: Xaa = Thr or Cys

<400> SEQUENCE: 5

Leu Gly Lys Phe Ser Gln Thr Cys Tyr Asn Xaa Ala Ile Xaa Gly Xaa
1 5 10 15

Val Leu Xaa Xaa Thr Cys Glu Arg Thr Asn Gly Gly Tyr Asn Xaa Xaa
20 25 30

Xaa Ile Asp Leu Asn Xaa Val Ile Glu Asn Val Asp Gly Xaa Leu Lys
35 40 45

Trp Gln Pro Ser Asn Phe Ile Glu Thr Cys Arg Asn Xaa Xaa Leu Ala
50 55 60

Gly Xaa Xaa Glu Leu Ala Ala Glu Cys Lys Thr Arg Ala Gln Gln Phe
65 70 75 80

Val Xaa Xaa Lys Ile Asn Leu Asp Asp His Ile Ala Asn Ile Asp Gly
85 90 95

Thr Leu Lys Tyr Glu
            100

<210> SEQ ID NO 6
<211> LENGTH: 101
<212> TYPE: PRT
<213> ORGANISM: Artificial Sequence
<220> FEATURE:
<223> OTHER INFORMATION: cyanovirin-N variant
<220> FEATURE:
<221> NAME/KEY: VARIANT
<222> LOCATION: 3, 48, 74, 84, 99
<223> OTHER INFORMATION: Xaa = Lys or Arg

<400> SEQUENCE: 6

Leu Gly Xaa Phe Ser Gln Thr Cys Tyr Asn Ser Ala Ile Gln Gly Ser
  1               5                  10                  15

Val Leu Thr Ser Thr Cys Glu Arg Thr Asn Gly Gly Tyr Asn Thr Ser
             20                  25                  30

Ser Ile Asp Leu Asn Ser Val Ile Glu Asn Val Asp Gly Ser Leu Xaa
         35                  40                  45

Trp Gln Pro Ser Asn Phe Ile Glu Thr Cys Arg Asn Thr Gln Leu Ala
 50                  55                  60

Gly Ser Ser Glu Leu Ala Ala Glu Cys Xaa Thr Arg Ala Gln Gln Phe
65                  70                  75                  80

Val Ser Thr Xaa Ile Asn Leu Asp Asp His Ile Ala Asn Ile Asp Gly
             85                  90                  95

Thr Leu Xaa Tyr Glu
            100

<210> SEQ ID NO 7
<211> LENGTH: 101
<212> TYPE: PRT
<213> ORGANISM: Artificial Sequence
<220> FEATURE:
<223> OTHER INFORMATION: cyanovirin-N variant

<400> SEQUENCE: 7

Leu Gly Lys Phe Ser Gln Thr Cys Tyr Asn Ser Ala Ile Gln Gly Ser
  1               5                  10                  15

Val Leu Thr Ser Thr Cys Glu Arg Thr Asn Gly Gly Tyr Asn Thr Ser
             20                  25                  30

Ser Ile Asp Leu Asn Ser Val Ile Glu Asn Val Asp Gly Ser Leu Lys
         35                  40                  45

Trp Gln Pro Ser Asn Phe Ile Glu Thr Cys Arg Asn Thr Cys Leu Ala
 50                  55                  60

Gly Ser Ser Glu Leu Ala Ala Glu Cys Lys Thr Arg Ala Gln Gln Phe
65                  70                  75                  80

Val Ser Thr Lys Ile Asn Leu Asp Asp His Ile Ala Asn Ile Asp Gly
             85                  90                  95

Thr Leu Lys Tyr Glu
            100

<210> SEQ ID NO 8
<211> LENGTH: 101
<212> TYPE: PRT
<213> ORGANISM: Artificial Sequence
<220> FEATURE:
<223> OTHER INFORMATION: cyanovirin-N variant

<400> SEQUENCE: 8

-continued

```
Leu Gly Lys Phe Ser Gln Thr Cys Tyr Asn Ser Ala Ile Cys Gly Ser
 1               5                  10                  15

Val Leu Thr Ser Thr Cys Glu Arg Thr Asn Gly Gly Tyr Asn Thr Ser
            20                  25                  30

Ser Ile Asp Leu Asn Ser Val Ile Glu Asn Val Asp Gly Ser Leu Lys
        35                  40                  45

Trp Gln Pro Ser Asn Phe Ile Glu Thr Cys Arg Asn Thr Gln Leu Ala
    50                  55                  60

Gly Ser Ser Glu Leu Ala Ala Glu Cys Lys Thr Arg Ala Gln Gln Phe
65                  70                  75                  80

Val Ser Thr Lys Ile Asn Leu Asp Asp His Ile Ala Asn Ile Asp Gly
                85                  90                  95

Thr Leu Lys Tyr Glu
            100
```

<210> SEQ ID NO 9
<211> LENGTH: 306
<212> TYPE: DNA
<213> ORGANISM: Artificial Sequence
<220> FEATURE:
<223> OTHER INFORMATION: synthetic construct

<400> SEQUENCE: 9

```
cttggtaaat tctcccagac ctgctacaac tccgctatcc agggttccgt tctgacctcc     60
acctgcgaac gtaccaacgg tggttacaac acctcctcca tcgacctgaa ctccgttatc    120
gaaaacgttg acggttccct gaaatggcag ccgtccaact tcatcgaaac ctgccgtaac    180
acccagctgg ctggttcctc cgaactggct gctgaatgca aaacccgtgc tcagcagttc    240
gtttccacca aaatcaacct ggacgaccac atcgctaaca tcgacggtac cctgaaatac    300
gaataa                                                               306
```

<210> SEQ ID NO 10
<211> LENGTH: 34
<212> TYPE: DNA
<213> ORGANISM: Artificial Sequence
<220> FEATURE:
<223> OTHER INFORMATION: primer

<400> SEQUENCE: 10

```
caactccgct atctgcggtt ccgttctgac ctcc                                 34
```

<210> SEQ ID NO 11
<211> LENGTH: 33
<212> TYPE: DNA
<213> ORGANISM: Artificial Sequence
<220> FEATURE:
<223> OTHER INFORMATION: primer

<400> SEQUENCE: 11

```
cctgccgtaa cacctgcctg gctggttcct ccg                                  33
```

<210> SEQ ID NO 12
<211> LENGTH: 306
<212> TYPE: DNA
<213> ORGANISM: Artificial Sequence
<220> FEATURE:
<223> OTHER INFORMATION: variant cyanovirin-N coding sequence for SEQ ID
      NO:7

<400> SEQUENCE: 12

```
cttggtaaat tctcccagac ctgctacaac tccgctatcc agggttccgt tctgacctcc     60
```

-continued

```
acctgcgaac gtaccaacgg tggttacaac acctcctcca tcgacctgaa ctccgttatc        120
gaaaacgttg acggttccct gaaatggcag ccgtccaact tcatcgaaac ctgccgtaac        180
acctgcctgg ctggttcctc cgaactggct gctgaatgca aaacccgtgc tcagcagttc        240
gtttccacca aaatcaacct ggacgaccac atcgctaaca tcgacggtac cctgaaatac        300
gaataa                                                                   306

<210> SEQ ID NO 13
<211> LENGTH: 306
<212> TYPE: DNA
<213> ORGANISM: Artificial Sequence
<220> FEATURE:
<223> OTHER INFORMATION: variant cyanovirin-N coding sequence for SEQ ID
      NO:8

<400> SEQUENCE: 13
cttggtaaat tctcccagac ctgctacaac tccgctatct gcggttccgt tctgacctcc         60
acctgcgaac gtaccaacgg tggttacaac acctcctcca tcgacctgaa ctccgttatc        120
gaaaacgttg acggttccct gaaatggcag ccgtccaact tcatcgaaac ctgccgtaac        180
acccagctgg ctggttcctc cgaactggct gctgaatgca aaacccgtgc tcagcagttc        240
gtttccacca aaatcaacct ggacgaccac atcgctaaca tcgacggtac cctgaaatac        300
gaataa                                                                   306
```

CYANOVIRIN VARIANT-POLYMER CONJUGATES

This application claims priority to U.S. provisional application Nos. 60/461,731, filed Apr. 9, 2003, and 60/435,950, filed Dec. 19, 2002, both of which are hereby incorporated by reference in their entirety.

STATEMENT OF GOVERNMENT RIGHTS

This invention was made with government support under the United States National Cancer Institute/Public Health Service Cooperative Research and Development Agreement (CRADA) No. 00837. The United States government may have certain rights in this invention.

FIELD OF THE INVENTION

The present invention relates to the field of protein-polymer conjugates. More specifically, the present invention relates to (i) variants of cyanovirin that are suitable for site-specific or site-selective conjugation to activated water-soluble polymers such as polyethylene glycols, (ii) cyanovirin variant-polymer conjugates, and (iii) methods for making and using such conjugates.

BACKGROUND OF THE INVENTION

Cyanovirin-N (CV-N) is a potent HIV-inactivating protein that was originally isolated and identified from aqueous extracts of the cultured cyanobacterium *Nostoc ellipsosporum* (U.S. Pat. No. 6,420,336). Since its identification, methods have been developed for the recombinant production of cyanovirin-N in *Escherichia coli* (Mori, T. et al., *Protein Expr. Purif.* 12:151-158, 1998). Cyanovirin-N is an 11 kDa protein consisting of a single 101-amino acid chain containing two intra-chain disulfide bonds. CV-N is an elongated, largely β-sheet protein that displays internal two fold pseudosymmetry and binds with high affinity and specificity to the HIV surface envelope protein, gp120 (Bewley, C. R. et al, *Nature Structural Biology* 5(7):571-578, 1998).

Despite its observed anti-viral activity, development of cyanovirin-N protein therapies has been hampered by its relatively short half-life after administration, as well as its in-vivo immunogenicity and potential toxic side effects. Most proteins, particularly relatively low molecular weight proteins introduced into the circulation, are cleared quickly from the mammalian subject by the kidneys. This problem may be partially overcome by administering large amounts of a therapeutic protein or through frequent dosing. However, higher doses of a protein can elicit antibodies that can bind and inactivate the protein and/or facilitate the clearance of the protein from the subject's body. In this way, repeated administration of such therapeutic proteins can essentially become ineffective. Additionally, such an approach may be dangerous since it can elicit an allergic response.

Various attempts to solve the problems associated with protein therapies include microencapsulation, liposome delivery systems, administration of fusion proteins, and chemical modification. The most promising of these to date is modification of a therapeutic protein by covalent attachment of poly(alkylene oxide) polymers, particularly polyethylene glycols ("PEG"). For example, Roberts, M. et al., *Adv. Drug Delivery Reviews* 54 (2002), 459-476, describes the covalent modification of biological macromolecules with PEG to provide physiologically active, non-immunogenic water-soluble PEG conjugates. Methods of attaching PEG to therapeutic molecules, including proteins, are also disclosed in, for example, U.S. Pat. Nos. 4,179,337, 5,122,614, 5,446,090, 5,990,237, 6,214,966, 6,376,604, 6,413,507, 6,495,659, and 6,602,498, each of which is incorporated herein by reference.

The hydrated random coil nature of PEG masks surface epitopes on proteins that would otherwise be recognized by the immune system. As a result, attachment of PEG to a therapeutic protein can slow its rejection by the body, reduce protein, cell and bacterial adsorption, and increase the hydrodynamic radius of the protein to reduce glomerular filtration and kidney clearance. Several proteins have been modified by addition of PEG, including adenosine deaminase, L-asparaginase, interferon alpha 2b, superoxide dismutase, streptokinase, tissue plasminogen activator (tPA), urokinase, uricase, hemoglobin, interleukins, interferons, TGF-β, EGF, and other growth factors, to name a few (Nucci et al, *Adv. Drug Delivery Rev.* 4:133-151,1991). Such modification has provided extended half-lives of the proteins, reduced toxicity and/or immunogenicity, improved pharmacokinetics, and greater solubility compared to the unconjugated proteins.

Unfortunately, attachment of polymer chains such as PEG to a protein does not, in all cases, result in a protein having improved therapeutic properties. During PEGylation, if the modification of the protein goes substantially to completion, i.e. if all or a majority of the available reactive sites on the protein are PEGylated, a significant amount of the bioactivity of the protein can be lost. For example, as described below, PEGylation of the lysine residues of cyanovirin-N produced conjugates having no significant bioactivity.

Partial PEGylation of a protein can reduce this impact on bioactivity. However, a drawback of partial modification, when using a non-selective process, is the production of a heterogeneous mixture of PEGylated protein, having a statistical distribution of various PEGylated species, e.g., mixtures of mono-PEGylated, di-PEGylated species and the like, at various available residue positions within the protein. It is difficult to predict with any certainty the impact of such attachment upon the properties of the resulting conjugate composition (e.g., stability, bioactivity, toxicity, etc.).

Moreover, such randomly PEGylated conjugate compositions, containing a mixture of PEGylated proteins differing in both the number and position of the PEG groups attached, often cannot be reproducibly prepared. Such mixtures of diversely modified proteins are generally not suitable for use as pharmaceutical compositions.

Purification and isolation of a defined class of PEGylated proteins from such a mixture, even when feasible, involves time-consuming and expensive procedures which result in an overall reduction in the yield of the specific PEGylated protein of interest. Separation of positional isomers, i.e. conjugates containing the same number of PEG moieties but at different positions, can be especially difficult, since they have similar molecular weights. These complications can render use of non-specifically PEGylated proteins economically impractical.

Due to the above described drawbacks to many of the existing PEGylation approaches, there remains a need to develop approaches for attaching PEG to specific molecules, such as cyanovirin, to provide PEG conjugates that significantly retain their bioactivity while exhibiting reduced systemic toxicity and improved circulating half-life, and result in pharmaceutical compositions having well-defined components.

SUMMARY OF THE INVENTION

In part to address these and other difficulties, the present invention provides defined protein-polymer conjugates which comprise a water soluble polymer covalently attached to a particular cyanovirin-N protein variant. Such variants, as provided herein, are polypeptides modified to include a defined number of reactive sites, preferably one to four, and more preferably one or two, that may be selectively coupled to a water-soluble polymer.

Particular embodiments of the cyanovirin-N variants of the invention include antiviral polypeptides having at least 70% sequence identity to native cyanovirin-N (SEQ ID NO. 1) and having a cysteine substitution or insertion at at least one position selected from the group consisting of 5, 9-21, 25, 29-40, 45-49, 52, 57, 59-72, 79-91, 96-101, the C-terminus, and the N-terminus. Alternatively, the polypeptide may have an arginine substitution at at least four residues selected from the group consisting of 3, 48, 74, 84, and 99.

In selected embodiments, the antiviral peptide having one or more of the above substitutions or insertions has at least at least 80%, more preferably at least 90%, and most preferably at least 95% homology to SEQ ID NO: 1. In one embodiment, the polypeptide includes a modification as described above but otherwise corresponds in sequence to that presented herein as SEQ ID) NO. 1 (native cyanovirin-N).

Preferred sites for cysteine substitutions or insertions include positions 5, 9-21, 25, 29-40, 45-49, 52, 57, 59-72, 79-91, 96-101, the C-terminus, and the N-terminus, and more preferably positions 9-21, 29-40, 45-49, 57, 59-72, 79-91, and 96-101, of SEQ ID NO: 1. The number of such cysteine insertions or, preferably, substitutions is preferably one to four, more preferably one or two. In further embodiments, the polypeptide is a polypeptide corresponding to SEQ ID NO: 1 but having one or two cysteine insertions or, preferably, substitutions at a position selected from 10-20, 31-39, 46-48, 60-71, 80-90, and 97-100, more preferably selected from 11, 14, 16, 19, 20, 31, 32, 33, 38, 46, 61, 62, 67, 68, 82, and 83. Particularly preferred positions include position 62 or position 14, where the polypeptide is substituted at either or both of these positions.

Such polypeptides include those having substitutions as represented in SEQ ID NOs: 2-6, presented in the Sequence Table at the end of this specification, and discussed further below. Preferably one to four, one to two, or one such substitution is included, and the polypeptide otherwise has at least 70%, preferably at least 80%, more preferably at least 90%, and most preferably at least 95% homology to SEQ ID NO: 1. In one embodiment, the polypeptide otherwise corresponds to SEQ ID NO: 1. In selected embodiments, the polypeptide has the sequence SEQ ID NO: 6 or SEQ ID NO: 7.

The conjugates of the invention may also include an antiviral fragment of a CV-N variant polypeptide as described above, comprising at least nine, preferably at least twenty, and more preferably at least forty, contiguous amino acids of such a polypeptide, and spanning at least one of the substitutions or insertions described above. The fragment may include a region corresponding to residues 41-78 of native cyanovirin-N (SEQ ID NO: 1) and including at least one of the substitutions or insertions described above. Preferably, the fragment includes a cysteine substitution at a residue selected from 11, 14, 16, 19, 20, 31, 32, 33, 38, 46, 61, 62, 67, 68, 82, and 83 of SEQ ID NO: 1.

In one embodiment, the fragment includes a cysteine substitution at position 62.

According to another aspect of the invention, provided is a polynucleotide encoding an antiviral cyanovirin-N polypeptide variant of the invention, or fragment thereof, as. disclosed above, along with recombinant vectors and transformed host cells comprising such polynucleotides. In preferred embodiments, the polynucleotide encodes a polypeptide corresponding to SEQ ID NO: 1 but having one or two cysteine insertions or, preferably, substitutions at a position selected from 10-20, 31-39, 46-48, 60-71, 80-90, and 97-100, more preferably selected from 11, 14, 16, 19, 20, 31, 32, 33, 38, 46, 61, 62, 67, 68, 82, and 83. Particularly preferred positions include position 62 or position 14, where the polypeptide is substituted at either or both of these positions. In selected embodiments, the polynucleotide includes the coding sequence shown in SEQ ID NO: 12 or SEQ ID NO: 13 of the Sequence Table enclosed herein.

In yet another aspect, provided are polymer conjugates of these variants. Specifically, the polymer conjugate comprises an antiviral polypeptide variant as described above, covalently attached to at least one water-soluble polymer. In one particularly preferred embodiment, the water soluble polymer is a poly(alkylene oxide) such as polyethylene glycol (PEG), covalently attached at a cysteine substitution or insertion site. According to yet another embodiment, the water-soluble polymer is a polyethylene glycol covalently attached at a cysteine insertion or substitution site of a cyanovirin-N variant.

More particularly, the invention provides an antiviral polypeptide-polymer conjugate, which comprises (i) an antiviral polypeptide having at least 70% sequence identity to native cyanovirin-N (SEQ ID NO. 1), and having a cysteine substitution or insertion at at least one position selected from the group consisting of 5, 9-21, 25, 29-40, 45-49, 52, 57, 59-72, 79-91, 96-101, the C-terminus, and the N-terminus, or an arginine substitution at at least four residues selected from the group consisting of 3, 48, 74, 84, and 99; or a fragment thereof comprising at least nine amino acids and including at least one said substitution or insertion; and (ii) a water soluble polymer covalently attached to the polypeptide or fragment thereof at at least one site of such substitution or insertion.

Preferably, the water-soluble polymer is attached at a site of cysteine insertion or, more preferably, substitution as recited above. Particularly preferred sites of such substitution include positions 11, 14, 16, 19, 20, 31, 32, 33, 38, 46, 61, 62, 67, 68, 82, and 83 of SEQ ID NO: 1.

The water soluble polymer may be attached via various linkages, e.g. an amide, secondary amine, ester, disulfide, ether, thioether, urea, or carbamate linkage.

The conjugate typically includes one to four, preferably one or two, attached water-soluble polymers. In selected embodiments, one such polymer is attached. Preferred types of water soluble polymers include poly(alkylene glycols), poly(acrylomorpholine), poly(vinylpyrolidone), poly(vinylalcohol), and copolymers thereof; particularly preferred are polyalkylene oxides, such as polyethylene glycol (PEG). The polymer may have a range of molecular weights; e.g. the average molecular weight may be in the range of about 350 daltons to about 200,000 daltons, preferably in the range of about 2,000 to about 200,000 daltons, and more preferably in the range of about 5,000 to about 40,000 daltons.

PEG polymers included in the conjugates may have various structural morphologies, e.g. linear polyethylene glycol, end-capped polyethylene glycol, branched polyethylene glycol, and/or forked polyethylene glycol. The polymer may also include one or more linkages which are degradable under physiological conditions in vivo.

In one embodiment, the conjugate comprises a PEG polymer attached to a cysteine residue substituted at position 62 of a polypeptide corresponding to SEQ ID NO. 1. The average molecular weight of the polymer is preferably in the range of 10 to 40 kDa, more preferably 20 to 30, and most preferably 25 to 35 kDa. In one embodiment, the average molecular weight is about 30,000 Daltons.

In a further aspect of the invention, provided is a pharmaceutical composition comprising a therapeutically or prophylactically effective amount of a protein-polymer conjugate as described above and a pharmaceutically acceptable carrier. The pharmaceutical compositions of the invention can be formulated for delivery via any one of the following routes: intravenous injection, subcutaneous injection, intramuscular injection, intracerebral vein injection, inhalation, intranasal administration, topical administration, transdermal administration, oral administration, ocular administration, vaginal administration, and rectal administration.

Also provided is a polymer-cyanovirin variant conjugate as described above affixed to or in combination with a particle, magnetic bead, flow through matrix, condom, diaphragm, cervical cap, vaginal ring, sponge, foam, or gel.

In yet another aspect, provided is a method for the treatment, prevention or mitigation of infection of at least one high mannose envelope virus, by administering a pharmaceutical composition as described above to a subject in need thereof The conjugates of the invention can be used, for example, to treat, prevent, or mitigate infection of viruses such as immunodeficiency virus, influenza virus, measles virus, herpes virus 6, marburg virus, and ebola virus.

These and other aspects of the invention will become apparent to one of skill in the art upon reading the disclosure in its entirety, in combination with the accompanying drawings.

DEFINITIONS

Figure 1:
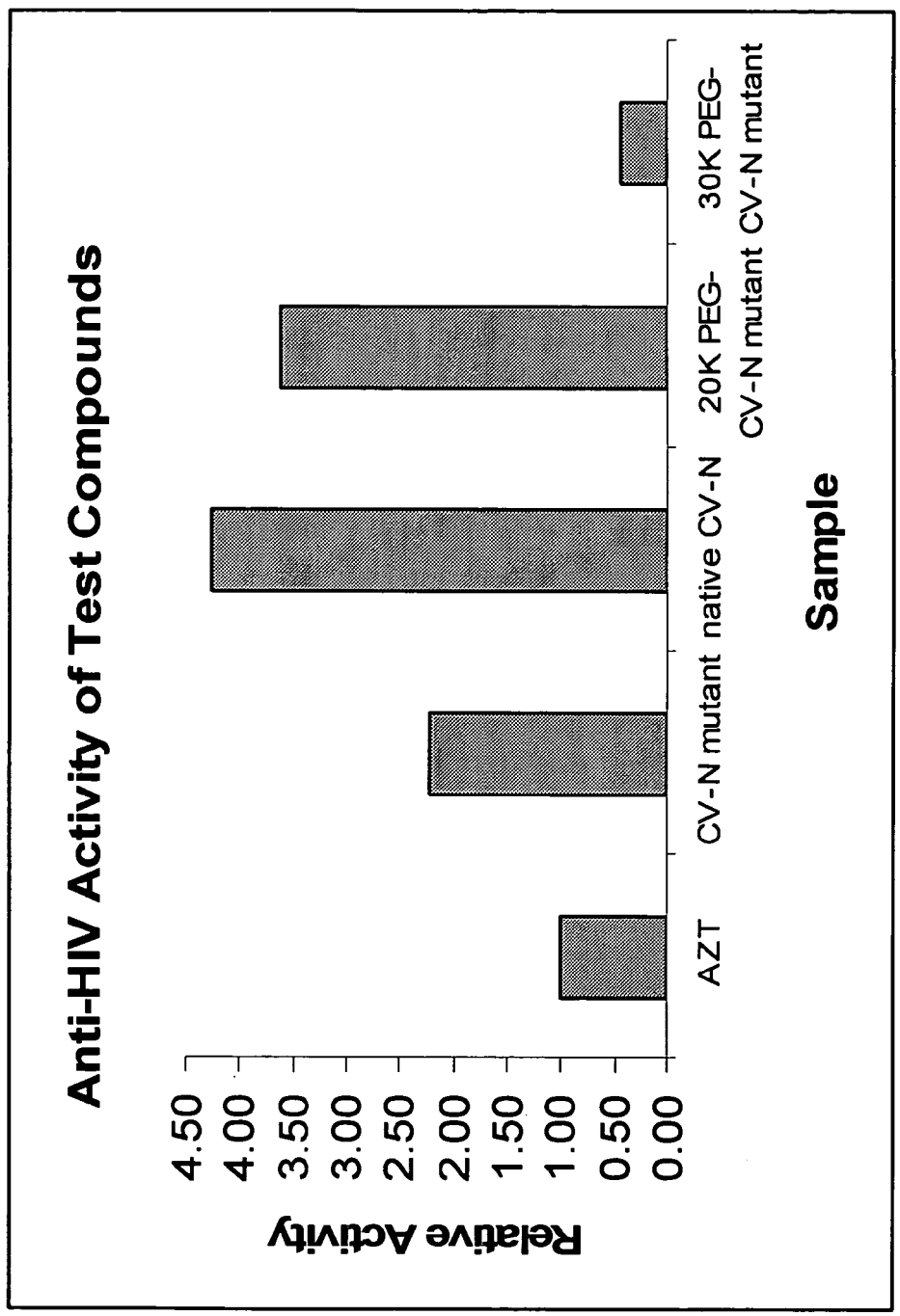
FIG. 1 is a bar graph demonstrating the activity of native cyanovirin-N, an illustrative CV-N positional mutant, and PEGylated-CV-N mutants relative to AZT in an in vitro anti-HIV assay.

The following terms as used herein have the meanings indicated.

As used in the specification, and in the appended claims, the singular forms "a", "an", "the", include plural referents unless the context clearly dictates otherwise. "PEG" or "polyethylene glycol", as used herein, is meant to encompass any water-soluble poly(ethylene oxide). Most typically, PEGs for use in the present invention will contain the following structure —$CH_2CH_2O(CH_2CH_2O)_nCH_2CH_2$—, where n is at least 2, and the terminal groups or actual architecture of the overall PEG moiety may vary. "PEG" means a polymer that contains a majority, that is to say, greater than 50%, of subunits that are —$CH_2CH_2O$—. One commonly employed PEG is end-capped PEG, wherein one terminus of the PEG is capped with a relatively inactive or inert group, typically an alkoxy group such as methoxy (—$OCH_3$), while the at least one other terminus is a hydroxyl or activated group that can be subjected to further chemical modification. Specific PEG forms for use in the invention include PEGs having a variety of molecular weights, structures or geometries (branched, multi-armed, linear, forked PEGs, and the like), to be described in greater detail below.

"Nominal average molecular weight", in the context of a water-soluble, non-naturally occurring polymer of the invention such as PEG, refers to the mass average molecular weight of polymer, typically determined by size exclusion chromatography, light scattering or intrinsic velocity in 1,2,4-trichlorobenzene. The polymers of the invention are typically polydisperse, possessing low polydispersity values of less than about 1.05.

The term "active" or "activated", when used in conjunction with a particular functional group, refers to a reactive functional group that reacts readily with an electrophile or a nucleophile on another molecule. This is in contrast to those groups that require strong catalysts or highly impractical reaction conditions in order to react (i.e., a "non-reactive" or "inert" group).

The terms "protected" and "protecting group" or "protective group" refer to the presence of a moiety (i.e., the protecting group) that prevents or blocks reaction of a particular chemically reactive functional group in a molecule under certain reaction conditions. The protecting group will vary depending upon the type of chemically reactive group being protected as well as the reaction conditions to be employed and the presence of additional reactive or protecting groups in the molecule, if any. Protecting groups known in the art can be found in Greene, T.

W. et al., PROTECTIVE GROUPS IN ORGANIC SYNTHESIS, 3rd ed., John Wiley & Sons, Inc., New York, N.Y. (1999).

As used herein, the term "functional group" or any synonym thereof is meant to encompass protected forms thereof The term "linkage" or "linker" (L) is used herein to refer to an atom or a collection of atoms optionally used to link interconnecting moieties such as a terminus of a polymer segment and a reactive group or center on a protein, polypeptide, small molecule or surface. A linker may be hydrolytically stable or may include a physiologically hydrolyzable or enzymatically degradable linkage.

"Alkyl" refers to a saturated hydrocarbon chain, typically ranging from about 1 to 15 atoms in length. Such hydrocarbon chains may be branched or straight chain, although typically straight chain is preferred. Exemplary alkyl groups include ethyl, propyl, butyl, pentyl, 1-methylbutyl, 1-ethylpropyl, 3-methylpentyl, and the like.

"Lower alkyl" refers to an alkyl group containing from 1 to 6 carbon atoms, and may be straight chain or branched, as exemplified by methyl, ethyl, n-butyl, i-butyl, t-butyl.

"Alkenyl" refers to a hydrocarbon chain having one or more carbon-carbon double bonds, typically ranging from about 1 to 15 atoms in length. Such hydrocarbon chains may be branched or straight chain, although typically straight chain is preferred.

"Cycloalkyl" refers to a saturated cyclic hydrocarbon, including bridged, fused, or spiro cyclic compounds, preferably made up of 3 to about 12 carbon atoms, more preferably 3 to about 8. "Cycloalkenyl" refers to such a group having one or more carbon-carbon double bonds.

"Non-interfering substituents" are those groups that, when present in a molecule, are typically non-reactive with other functional groups contained within the molecule.

The term "substituted", with reference to an alkyl, alkenyl, cycloalkyl, or cycloalkenyl group, refers to such a group substituted with one or more non-interfering substituents, such as, but not limited to, C3-C8 cycloalkyl, e.g., cyclopropyl, cyclobutyl, and the like; cyano; alkoxy, lower phenyl; substituted phenyl; and the like.

"Alkoxy" refers to an —O-R group, wherein R is optionally substituted alkyl or alkenyl, preferably C1-C6 (e.g., methoxy, ethoxy, propyloxy, etc.).

"Aryl" refers a group containing one or more aromatic rings, each having 5 or 6 ring carbon atoms. The term includes multiple aryl rings that may be fused, as in naphthyl, or unfused, as in biphenyl. Aryl rings may also be fused or unfused with one or more cyclic hydrocarbon, heteroaryl, or heterocyclic rings.

"Substituted aryl" is aryl having one or more non-interfering groups as a substituent. For substitutions on a phenyl ring, the substituents may be in any orientation (i.e., ortho, meta or para).

"Heteroaryl" is an aryl group containing from one to four heteroatoms, preferably N, O, or S, or a combination thereof Examples include furan, pyrrole, pyridine, imidazole, and fused systems such as indole. Heteroaryl rings may also be fused with one or more cyclic hydrocarbon, heterocyclic, aryl, or heteroaryl rings. "Substituted heteroaryl" refers to heteroaryl having one or more non-interfering groups as substituents.

"Aralkyl" refers to an alkyl, preferably lower ($C_1$-$C_4$, more preferably $C_1$-$C_2$) alkyl, substituent which is further substituted with an aryl group; examples are benzyl and phenethyl.

"Heterocycle" or "heterocyclic" refers to one or more rings of 5-12 atoms, preferably 5-7 atoms, with or without unsaturation or aromatic character, having at least one ring atom which is not a carbon. Preferred heteroatoms include sulfur, oxygen, and nitrogen. Examples of aromatic heterocycles are given above. Non-aromatic heterocycles include, for example, pyrrolidine, piperidine, piperazine, and morpholine.

"Substituted heterocycle" is a heterocycle having one or more side chains formed from non-interfering substituents.

"Electrophile" refers to an atom or collection of atoms having an electrophilic center, i.e., a center that is electron seeking, capable of reacting with a nucleophile.

A "physiologically hydrolyzable" bond is a relatively weak bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include but are not limited to carboxylate ester, phosphate ester, anhydrides, acetals, ketals, acyloxyalkyl ether, imines, orthoesters, peptides and oligonucleotides.

An "enzymatically degradable linkage" means a linkage that is subject to degradation by one or more enzymes.

A "hydrolytically stable" linkage or bond refers to a chemical bond, typically a covalent bond, that is substantially stable in water; that is to say, it does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes, and the like. Generally, a hydrolytically stable linkage is one that exhibits a rate of hydrolysis of less than about 1-2% per day under physiological conditions. Hydrolysis rates of representative chemical bonds can be found in most standard chemistry textbooks.

"Pharmaceutically acceptable excipient or carrier" refers to an excipient that may optionally be included in the compositions of the invention and that causes no significant adverse toxicological effects to the subject.

"Pharmacologically effective amount" or "physiologically effective amount" is the amount of a polymer-cyanovirin variant conjugate present in a therapeutic composition as described herein that is needed to provide a desired level of active agent in the bloodstream or in the target tissue. The precise amount will depend upon numerous factors, e.g., the particular drug or therapeutic agent, the components and physical characteristics of the therapeutic composition, intended patient population, patient considerations, and the like, and can readily be determined by one skilled in the art, based upon the information provided herein.

"Bifunctional" in the context of a polymer of the invention refers to a polymer possessing two reactive functional groups which may be the same or different.

"Multifunctional" in the context of a polymer of the invention means a polymer having 3 or more functional groups attached thereto, where the functional groups may be the same or different. Multifunctional polymers of the invention will typically comprise from about 3-100 functional groups, or from 3-50 functional groups, or from 3-25 functional groups, or from 3-15 functional groups, or from 3 to 10 functional groups, or will contain 3, 4, 5, 6, 7, 8, 9 or 10 functional groups attached to the polymer backbone. The term "polypeptide polymer conjugate" refers to a polypeptide such as cyanovirin (or a bioactive fragment thereof) covalently linked to at least one water-soluble polymer.

"Antiviral activity", as used herein in reference to a cyanovirin variant, fragment or polymer conjugate, signifies a measurable degree of cyanovirin antiviral activity (e.g., from at least about 15% to about 100% or more of the biological activity of native cyanovirin).

"Amino acid" refers to any compound containing both an amino group and a carboxylic acid group. Although the amino group most commonly occurs at the position adjacent (α) to the carboxy function, the amino group may be positioned at any location within the molecule. The amino acid may also contain additional functional groups, such as amino, thio, carboxyl, carboxamide, imidazole, etc. An amino acid may be synthetic or naturally occurring, and may be in either its racemic or optically active (D- or, preferably, the naturally occurring L-) form.

"Nucleic acid" refers to deoxyribonucleic acid (DNA) or ribonucleic acid (RNA).

The term "expression" refers to the transcription of a gene to produce the corresponding mRNA and translation of this mRNA to produce the corresponding gene product (i.e., a peptide, polypeptide, or protein). The term "expression of antisense RNA" refers to the transcription of a DNA to produce a first RNA molecule capable of hybridizing to a second RNA molecule. Formation of the RNA-RNA hybrid inhibits translation of the second RNA molecule to produce a gene product.

"Hybridization" refers to the ability of a strand of nucleic acid to join with a complementary strand via base pairing. Hybridization occurs when complementary nucleic acid sequences in the two nucleic acid strands contact one another under appropriate conditions.

The phrase "operably linked" refers to the functional spatial arrangement of two or more nucleic acid regions or nucleic acid sequences. For example, a promoter region may be positioned relative to a nucleic acid sequence such that transcription of a nucleic acid sequence is directed by the promoter region. Thus, a promoter region is "operably linked" to the nucleic acid sequence.

"Polyadenylation signal" or "polyA signal" refers to a nucleic acid sequence located 3' to a coding region that promotes the addition of adenylate nucleotides to the 3' end of the MRNA transcribed from the coding region.

A "regulatory sequence" refers to a nucleotide sequence located upstream (5'), within, or downstream (3')to a coding sequence. Transcription and expression of the coding sequence is typically impacted by the presence or absence of the regulatory sequence. "Transcription" refers to the process of producing an RNA copy from a DNA template.

The term "promoter" or "promoter region" refers to a nucleic acid sequence, usually found upstream (5')to a coding sequence, which is capable of directing transcription of a nucleic acid sequence into mRNA. The promoter or promoter region typically provide a recognition site for RNA polymerase and the other factors necessary for proper initiation of transcription. As contemplated herein, a promoter or promoter region includes variations of promoters derived by inserting or deleting regulatory regions, subjecting the promoter to random or site-directed mutagenesis, etc. The activity or strength of a promoter may be measured in terms of the amounts of RNA it produces, or the amount of protein accumulation in a cell or tissue, relative to a promoter whose transcriptional activity has been previously assessed.

The term "protein" or "polypeptide" includes any molecule that comprises a chain of five or more amino acids. It is well known in the art that proteins may undergo modification, including post-translational modifications, such as, but not limited to, disulfide bond formation, glycosylation, phosphorylation, or oligomerization. Thus, as used herein, the term "protein" or "peptide molecule" includes any protein that is modified by any biological or non-biological process.

A "protein fragment" is a peptide or polypeptide molecule whose amino acid sequence comprises a subset of the amino acid sequence of the original protein. A protein or fragment thereof that comprises one or more additional peptide regions not derived from that protein is a "fusion" protein.

A "protein variant" is a protein whose amino acid sequence has been modified from its native amino acid sequence. Typical changes include amino acid substitutions, additions, and/or deletions, as well as the fusion of two sequences not normally connected.

The nomenclature used to describe polypeptides and proteins herein follows the conventional practice, wherein the amino group is assumed to be to the left and the carboxyl group to the right in each amino acid in the peptide. Amino- and carboxyl-terminal groups, although often not specifically shown, will be understood to be in the form they would assume at physiological pH values (i.e. $—NH_3^+$ and $—C(O)(O^-)$, unless otherwise specified.

"Recombinant vector" refers to any agent such as a plasmid, cosmid, virus, autonomously replicating sequence, phage, or linear single-stranded, circular single-stranded, linear double-stranded, or circular double-stranded DNA or RNA nucleotide sequence. The recombinant vector may be derived from any source and is capable of genomic integration or autonomous replication.

"Substantially homologous" refers to two sequences that are at least 90% identical in sequence, as measured by the BestFit program described herein (Version 10; Genetics Computer Group, Inc., University of Wisconsin Biotechnology Center, Madison, Wis.), using default parameters.

Two or more polynucleotide or polypeptide fragments have at least a given percent "sequence identity" if their nucleotide bases or amino acid residues are identical, respectively, in at least the specified percent of total base or residue position, when the two or more fragments are aligned such that they correspond to one another using a computer program such as BestFit or ALIGN. (The ALIGN program is found in the FASTA version 1.7 suite of sequence comparison programs, Pearson and Lipman, 1988; Pearson, 1990).

A modified sequence is said to "correspond to" a given sequence if it differs from the sequence only at positions specifically noted.

"Substantially purified" refers to a molecule separated from substantially all other molecules normally associated with it in its native state. More preferably a substantially purified molecule is the predominant species present in a preparation. A substantially purified molecule may be greater than 60% free, preferably 75% free, more preferably 90% free, and most preferably 95% free from the other molecules (exclusive of solvent) present in the natural mixture. The term "substantially purified" is not intended to encompass molecules present in their native state.

A "vector" refers to a plasmid, cosmid, bacteriophage, or virus that carries exogenous DNA into a host organism.

"Transformation" refers to the introduction of nucleic acid into a recipient host. The term "recombinant host cells", "host cells", or "host" refers to bacteria cells, fungi, animals or animal cells, plants or seeds, or any plant parts or tissues including plant cells, protoplasts, calli, roots, tubers, seeds, stems, leaves, seedlings, embryos, and pollen. The terms include the immediate subject cell and the progeny thereof It is understood that not all progeny are exactly identical to the parental cell, due to chance mutations or differences in environment. However, such altered progeny are included in these terms, so long as the progeny retain the characteristics relevant to those conferred on the originally transformed cell. In the present case, for example, such a characteristic might be the ability to produce recombinant CV-N or a variant thereof.

DETAILED DESCRIPTION OF THE INVENTION

I. Overview of the Invention

The invention is directed, in one aspect, to CV-N proteins which are modified to have only particular sites available for conjugation to a water soluble polymer, such as PEG. Replacement or insertion of a native CV-N amino acid with a cysteine residue, for example, allows site-specific modification of the particular cysteine residue using a sulfhydryl-specific PEG reagent, such as a PEG-maleimide or PEG-orthopyridyl disulfide. In this way, PEG-cyanovirin-variants having well-defined PEGylation position(s) can be prepared.

The preparation of illustrative cyanovirin variants of the invention is described in Examples 2-5. These variants were generated using a PCR based method, although any of a number of genetic engineering techniques can be employed.

The invention is further directed to conjugates prepared from such modified proteins. As described below, the CV-N variants of the invention, when PEGylated, can be purified to produce well-characterized, high purity PEG-CV-N variant compositions that possess significant antiviral activity, as well as reduced toxicity and immunogenicity and longer circulation time in vivo relative to native CV-N.

II. Cyanovirin-N Protein Variants

The variants are designed for the specific chemical attachment of one or more water-soluble polymers in a manner effective to retain the antiviral properties of the resulting polymer conjugate. A general discussion of amino acid substitution in proteins will be followed by a description of the preferred CV-N variants of the invention.

A. Amino Acid Substitutions

It is well known in the art that one or more amino acids in a native sequence can be substituted with other amino acid(s) having similar charge and polarity, i.e., a conservative amino acid substitution, resulting in a silent change. Conservative substitutions for an amino acid within the native polypeptide sequence can be selected from other members of the class to which the amino acid belongs.

The 20 amino acids found in naturally occurring proteins can be generally classified as polar (S, T, C, Y, D, N, E, Q, R, H, K) or non-polar (G, A, V, L, I, M, F, W, P). They can be further classified into four major classes; namely, acidic, basic, neutral/polar and neutraunonpolar, where the first three classes fall under the general heading of "polar" above. These four classes have the following characteristics:

Acidic: A significant percentage (e.g. at least 25%) of molecules are negatively charged (due to loss of H+ion) in aqueous solution at physiological pH. Basic: A significant percentage (e.g. at least 25%) of molecules are positively charged (due to association with H+ion) in aqueous solution at physiological pH. Both acidic and basic residues are attracted by aqueous solution, so as to seek outer surface positions in the conformation of a peptide in aqueous medium at physiological pH.

Neutral/polar: The residues are uncharged at physiological pH but are also attracted by aqueous solution, so as to seek outer surface positions in the conformation of a peptide in aqueous medium.

Neutral/non-polar: The residues are uncharged at physiological pH and are repelled by aqueous solution, so as to seek internal positions in the conformation of a peptide in aqueous medium. These residues are also designated "hydrophobic".

Amino acid residues can be further subclassified as cyclic/noncyclic and aromatic/nonaromatic, with respect to the side chain substituent groups of the residues, and as small or large. The residue is considered small if it contains a total of 4 carbon atoms or less, inclusive of the carboxyl carbon. Subclassification of the naturally occurring protein amino acids according to the foregoing scheme is as follows:

Acidic: Aspartic acid and Glutamic acid
Basic/noncyclic: Arginine and Lysine
Basic/cyclic: Histidine
Neutral/polar/small: Threonine, Serine and Cysteine
Neutral/polar/large/nonaromatic: Asparagine and Glutamine
Neutral/polar/large/aromatic: Tyrosine
Neutral/non-polar/small: Alanine
Neutral/non-polar/large/nonaromatic: Valine, Isoleucine, Leucine, and Methionine
Neutral/non-polar/large/aromatic: Phenylalanine and Tryptophan Proline, technically falling within the group neutral/non-polar/large/cyclic and nonaromatic, is considered a special case due to its known effects on the secondary conformation of peptide chains, and is not, therefore, included in this defined group, but is regarded as a group of its own.

The role of the hydropathic index of amino acids in conferring interactive biological function on a protein may be considered. See, for example, Kyte and Doolittle, *J. Mol. Biol.* 157:105-132 (1982). It is accepted that the relative hydropathic character of amino acids contributes to the secondary structure of the resultant protein, which in turn defines the interaction of the protein with other molecules, e.g., enzymes, substrates, receptors, DNA, antibodies, antigens, etc. It is also understood in the art that the substitution of like amino acids may be made effectively on the basis of hydrophilicity, as the greatest local average hydrophilicity of a protein is known to correlate with a biological property of the protein. See, for example, U.S. Pat. No. 4,554,101.

Each amino acid has been assigned a hydropathic index and a hydrophilic value, as shown in Table 1.

TABLE 1

Amino Acid Hydropathic Indices and Hydrophilic Values

| Amino acid | Hydropathic Index | Hydrophilic Value |
| --- | --- | --- |
| Alanine | +1.8 | −0.5 |
| Cysteine | +2.5 | −1.0 |
| Aspartic acid | −3.5 | +3.0 ± 1 |
| Glutamic acid | −3.5 | +3.0 ± 1 |
| Phenylalanine | +2.8 | −2.5 |
| Glycine | −0.4 | 0 |
| Histidine | −3.2 | −0.5 |
| Isoleucine | +4.5 | −1.8 |
| Lysine | −3.9 | +3.0 |
| Leucine | +3.8 | −1.8 |
| Methionine | +1.9 | −1.3 |
| Asparagine | −3.5 | +0.2 |
| Proline | −1.6 | −0.5 ± 1 |
| Glutamine | −3.5 | +0.2 |
| Arginine | −4.5 | +3.0 |
| Serine | −0.8 | +0.3 |
| Threonine | −0.7 | −0.4 |
| Valine | +4.2 | −1.5 |
| Tryptophan | −0.9 | −3.4 |
| Tyrosine | −1.3 | −2.3 |

It is known in the art that certain amino acids may be substituted by other amino acids having a similar hydropathic or hydrophilic index, score or value, and result in a protein with similar biological activity. The substitution of amino acids whose hydropathic indices or hydrophilic values are within ±2 is preferred, those within ±1 are more preferred, and those within ±0.5 are most preferred.

As outlined above, conservative amino acid substitutions are therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine/lysine; glutamate/aspartate; serine/threonine; glutamine/asparagine; and valine/leucine/isoleucine.

The CV-N variants of the invention may also include commonly encountered amino acids which do not occur naturally in proteins, such as β-alanine, other omega-amino acids, such as 4-amino butyric acid, and so forth; α-aminoisobutyric acid (Aib), sarcosine (Sar), ornithine (Orn), citrulline (Cit), t-butylalanine (t-BuA), t-butylglycine (t-BuG), N-methylisoleucine (N-MeIle), phenylglycine (Phg), cyclohexylalanine (Cha), norleucine (Nle), cysteic acid (Cya), and methionine sulfoxide (MSO). These amino acids can also be classifed by the above scheme, as follows: Sar and β-Ala are neutral/non-polar/small; t-BuA, t-BuG, N-MeIle, Nle and Cha are neutral/ non-polar/large/nonaromatic; Orn is basic/noncyclic; Cya is acidic; Cit, Acetyl Lys, and MSO are neutral/polar/large/nonaromatic; and Phg is neutraUnon-polar/large/aromatic.

The various omega-amino acids are classified according to size as neutral/non-polar/small (β-Ala, 4-aminobutyric) or large (all others). Accordingly, conservative substitutions using these amino acids can be determined.

In a preferred aspect of the invention, biologically functional equivalents of the polypeptides or fragments thereof have about 25 or fewer conservative amino acid substitutions, more preferably about 15 or fewer conservative amino acid substitutions, and most preferably about 10 or fewer conservative amino acid substitutions. In further preferred embodiments, the polypeptide has between 1 and 10, between 1 and 7, or between 1 and 5 conservative substitutions. In selected embodiments, the polypeptide has 1, 2, 3, 4, or 5 conservative amino acid substitutions. In each case, the substitution(s) are preferably at the preferred amino acid residues of native CV-N noted below.

Non-conservative substitutions include additions, deletions, and substitutions that do not fall within the criteria given above for conservative substitutions. Non-conservative substitutions are preferably limited to regions of the protein which are remote, in a three-dimensional sense, from the mannose-binding sites that permit binding of CV-N to gp120 and other high mannose proteins (see below). Preferably, the protein has 15 or fewer non-conservative amino acid substitutions, more preferably 10 or fewer non-conservative amino acid substitutions. In further preferred embodiments, the polypeptide has fewer than 5 non-conservative substitutions. In selected embodiments, the polypeptide has 0, 1, 2, or 3 non-conservative amino acid substitutions.

B. Preferred Sites of Modification

In general, when choosing specific sites for modification, PEGylation sites are chosen such that the presence of the PEG molecule interferes minimally with active or binding site(s) of a protein. The effect of mutations located outside of the active site(s) are generally predictable in that they generally do not change the primary activity of the protein. In addition, solvent-accessible regions of the protein generally have limited or no interaction with other residues in the protein molecule; accordingly, mutations at these positions are unlikely to affect the conformation of any other amino acid in a protein.

In the present case, for modification of CV-N, residues having minimal interaction with the mannose-binding sites that permit binding of CV-N to target viral proteins such as gp120 are generally preferred. Recent studies suggest that these binding sites include a high affinity binding site, comprising residues 41-44, 50-56, and 74-78, and a low affinity binding site, comprising residues 1-7, 22-26, and 92-95. See e.g. C. A. Bewley et al., *J. Am. Chem. Soc.* 123:3892-3902 (May 2, 2001) and I. Botos et al., *J. Biol. Chem.* 277(37):34336-34342 (Sep. 13, 2002). (Amino acid positions refer to the amino acid residue position in the native cyanovirin-N protein, shown herein as SEQ ID NO: 1).

As noted above, a preferred mutation for site-specific modification is conversion of an amino acid to, or insertion of, a cysteine residue. Because cysteine residues in a native protein are generally involved in disulfide bonds, only the variant cysteine is generally available for modification, leading to high selectivity.

Another strategy employs conversion of the majority of lysine residues in the protein to arginine, preferably leaving a single lysine residue, or the N-terminus, available for substitution using an amine-reactive polymer reagent. This conversion generally has a minimal effect on the properties of the protein, since Lys/Arg is a conservative substitution, as discussed below. However, because it generally involves multiple substitutions, the cysteine substitution method noted above is generally preferred.

Accordingly, in one embodiment, a cysteine residue is substituted for a residue located in a region other than the binding sites noted above (or, alternatively, inserted in such a region). Such residues would include amino acids 9-21, 29-40, 45-49, 57, 59-72, 79-91, and 96-101; preferably amino acids 10-20, 31-39, 46-48, 60-71, 80-90, and 97-100, of SEQ ID NO: 1.

Particularly preferred for substitution with cysteine are glutamine, serine, and threonine residues. Gln and Ser are known glycosylation sites, and thus good candidates for polymeric attachment, while Ser and Thr are in the same general class (as described above) as Cys. Accordingly, preferred residues for Cys substitution would include 14 and 62 (Gln residues; 79 is also contemplated, although it is adjacent to a binding site), 11, 16, 20, 32, 33, 38, 46, 67, 68, and 82 (Ser residues), and 19, 31, 61, and 83 (Thr residues; again, residues 21, 57, and 97 are also contemplated, although each is near a binding site).

Particularly preferred mutant versions of CV-N include CV-N in which glutamine 62 or glutamine 14 is replaced by cysteine (Gln62Cys or Gln14Cys).

As noted above, substitution of lysine residues with arginine can also be a useful strategy for selective attachment. Accordingly, in one embodiment, all or all but one of the following residues is substituted with arginine: 3, 48, 74, 84, and 99. (When all of the lysine residues are substituted, reaction is directed to the N-terminus of the protein.) In this case, substitution within a binding site (such as at residue 3) is considered, since the substitution is conservative and will not entail attachment of a polymer.

These preferred sites of substitution are shown in SEQ ID NOs: 2-6 in the Sequence Table provided at the end of this specification. A protein containing any of the above noted substitutions is represented by SEQ ID NO: 2. (For example, in SEQ ID NO: 2, aa 3 is selected from Lys and Arg; aa 9 is selected from Tyr and Cys; aa 10 is selected from Asn and Cys; and so forth, as long as one such substitution is present.) A protein containing any of the above noted cysteine substitutions (i.e. at any of residues 9-21, 29-40, 45-49, 57, 59-72, 79-91, and 96-101) is represented by SEQ ID NO: 3. (For example, in SEQ ID NO: 3, aa 3 is Lys; aa 9 is selected from Tyr and Cys; aa 10 is selected from Asn and Cys; and so forth, as long as one such substitution is present.) A protein containing any of the above noted more preferred cysteine substitutions (i.e. at any of residues 10-20, 31-39, 46-48, 60-71, 80-90, and 97-100, which are boldfaced in the composite sequence) is represented by SEQ ID NO: 4. (For example, in SEQ ID NO: 4, aa 3 is Lys; aa 9 is Tyr; aa 10 is selected from Asn and Cys; aa 11 is selected from Ala and Cys, and so forth, as long as one such substitution is present.) A protein containing any of the above noted most preferred cysteine substitutions (i.e. at any of residues 11, 14, 16, 19,20, 31, 32, 33, 38,46, 61, 62, 67, 68, 82, and 83, which are which are boldfaced and italicized in the composite sequence) is represented by SEQ ID NO: 5. Finally, a protein containing any of the above noted Arg substitutions, but not the Cys substitutions, is represented by SEQ ID NO: 6.

The invention also provides cyanovirin-N protein variants having one or more amino acid residues, preferably a cysteine, added to the C-terminal or N-terminal portion of the native cyanovirin-N amino acid sequence.

Further substitutions which are contemplated include substitution of cysteine at one or more of the following positions: 24, 26, 27, 76, 77, and 78, or substitution of position 30 with Ala, Gln, or Val.

The cyanovirin-N protein variants modified as described herein preferably have at least about 70%, more preferably 80%, 90%, 95%, or 99%, sequence homology to native cyanovirin-N (SEQ ID NO: 1). Also contemplated are such cyanovirin-N protein variants in which non-essential or non-relevant amino acid residues have been added, replaced or deleted. Computerized means for designing and evaluating modifications in protein structure are known in the art; see e.g. Dahiyat and Mayo, *Science* 278:82-87 (1997).

The cyanovirin-N protein variants of the invention can be prepared by any method known in the art including random (via chemical mutagenesis or DNA shuffling) or specific mutagenesis of a native cyanovirin-N sequence to provide for one or more amino acid substitutions. A preferred method involves use of the QuikChange mutagenesis kit (Stratagene, La Jolla, Calif.) according to the manufacturer's protocol.

The cyanovirin-N protein variants of the invention can also be fusion proteins, e.g., they can include a "tagged" epitope to facilitate detection of the fusion protein. Alternatively, the fusion protein may provide regulatory, enzymatic, cell signaling, or intercellular transport functions.

The above-described cyanovirin-N protein variants may be produced via chemical synthesis, or more preferably, by expression in a suitable bacterial or eukaryotic host. Suitable methods for expression are described by Sambrook et al, supra, or similar texts. Fusion protein or peptide molecules of the invention are preferably produced via recombinant means.

Fragments of the proteins described above may also be conjugated to a water soluble polymer in the manner described herein. Such fragments include polypeptide molecules comprising at least about a contiguous 9 amino acid region, preferably comprising at least about a contiguous 10 amino acid region, even more preferably comprising at least about a contiguous 20, 25, 35, 50, 75 or 80 amino acid region of a cyanovirin-N protein variant as described above, where the amino acid region spans and includes at least one of the insertions or substitutions described above.

III. Nucleic Acid Molecules Encoding Cyanovirin-N Protein Variants

In another aspect of the invention, nucleic acid molecules encoding the cyanovirin-N protein variants of the invention, complements thereof, and nucleic acid molecules which hybridize thereto are also provided. Preferably, such nucleic acid molecules encode the preferred variants noted above, having, for example, one to four cysteine substitutions or insertions at a position selected from 9-21, 29-40, 45-49, 57, 59-72, 79-91, and 96-101 of SEQ ID NO: 1, more preferably from positions 10-20, 31-39, 46-48, 60-71, 80-90, and 97-100, and most preferably from positions 14 and 62 (Gln residues), 11, 16, 20, 32, 33,38, 46, 67, 68, and 82 (Ser residues), and 19, 21, 31, 57, 61, and 83 (Thr residues). Alternatively, the nucleic acid molecule may encode a variant in which all or all but one of the lysine residues of SEQ ID NO: 1 is converted to asparagine. As noted above, such variants are useful for site-specific attachment of water soluble polymers, to produce therapeutically useful CV-N-polymer conjugates.

The nucleic acid sequence can also encode a protein which differs from any of the above preferred proteins or peptides by virtue of one or more conservative amino acid changes, deletion, substitution, or addition, as described above. Preferably, the protein has at least 70% sequence homology, more preferably about 80%, 90%, or 95% sequence homology, with SEQ ID NO: 1.

The amino acid changes may be achieved by changing the codons of the nucleic acid sequence, according to the codons given in Table 2 below, and may be effected by mutating the nucleic acid sequence coding for the protein or peptide. Mutations to a nucleic acid sequence may be introduced in either a specific or random manner, both of which are well known to those of skill in the art of molecular biology. Mutations may include deletions, insertions, truncations, substitutions, fusions, shuffling of motif sequences, and the like. A myriad of site-directed mutagenesis techniques exist, typically using oligonucleotides to introduce mutations at specific locations in a structural nucleic acid sequence. Examples include single strand rescue, unique site elimination, nick protection, and PCR. Random or non-specific mutations may be generated by chemical agents (for a general review, see Singer and Kusmierek, *Ann. Rev. Biochem.* 52:655-693, 1982) such as nitrosoguanidine and 2-aminopurine; or by biological methods such as passage through mutator strains (Greener et al, *Mol Biotechnol.* 7:189-195, 1997).

It is understood that codons capable of coding for such conservative amino acid substitutions are known in the art.

Due to the degeneracy of the genetic code, different nucleotide codons may be used to code for a particular amino acid. A host cell often displays a preferred pattern of codon usage. Nucleic acid sequences are preferably constructed to utilize the codon usage pattern of the particular host cell. This generally enhances the expression of the nucleic acid sequence in a transformed host cell. Any of the above described nucleic acid sequences may be modified to reflect the preferred codon usage of a host cell or organism in which they are contained. Modification of a nucleic acid sequence for optimal codon usage in plants is described in U.S. Pat. No. 5,689,052. Additional variations in the nucleic acid sequences may encode proteins having equivalent or superior characteristics when compared to the proteins from which they are engineered.

Encoding of amino acids or changes thereto may be achieved using the codons of the nucleic acid sequence, according to the codons given in Table 2.

TABLE 2

Codon degeneracy of amino acids

| Amino acid | One letter | Three letter | Codons |
|---|---|---|---|
| Alanine | A | Ala | GCA GCC GCG GCT |
| Cysteine | C | Cys | TGC TGT |
| Aspartic acid | D | Asp | GAC GAT |
| Glutamic acid | E | Glu | GAA GAG |
| Phenylalanine | F | Phe | TTC TTT |
| Glycine | G | Gly | GGA GGC GGG GGT |
| Histidine | H | His | CAC CAT |
| Isoleucine | I | Ile | ATA ATC ATT |
| Lysine | K | Lys | AAA AAG |
| Leucine | L | Leu | TTA TTG CTA CTC CTG CTT |
| Methionine | M | Met | ATG |
| Asparagine | N | Asn | AAC AAT |
| Proline | P | Pro | CCA CCC CCG CCT |
| Glutamine | Q | Gln | CAA CAG |
| Arginine | R | Arg | AGA AGG CGA CGC CGG CGT |
| Serine | S | Ser | AGC AGT TCA TCC TCG TCT |
| Threonine | T | Thr | ACA ACC ACG ACT |
| Valine | V | Val | GTA GTC GTG GTT |
| Tryptophan | W | Trp | TGG |
| Tyrosine | Y | Tyr | TAC TAT |

For example, as described in Boyd et al., *Antimicrobial Agents and Chemotherapy* 41(7):1521-1530 (July 1997), the amino acid sequence of native CV-N was back-translated to a DNA sequence using an *E. coli* codon preference table, to give the following 5' to 3' coding sequence (SEQ ID NO: 9) (Genbank Acc. No. L48551):

```
CTTGGTAAAT TCTCCCAGAC CTGCTACAAC TCCGCTATCC AGGGTTCCGT  (SEQ ID NO: 9)

TCTGACCTCC ACCTGCGAAC GTACCAACGG TGGTTACAAC ACCTCCTCCA

TCGACCTGAA CTCCGTTATC GAAAACGTTG ACGGTTCCCT GAAATGGCAG

CCGTCCAACT TCATCGAAAC CTGCCGTAAC ACCCAGCTGG CTGGTTCCTC

CGAACTGGCT GCTGAATGCA AAACCCGTGC TCAGCAGTTC GTTTCCACCA

AAATCAACCT GGACGACCAC ATCGCTAACA TCGACGGTAC CCTGAAATAC

GAATAA
```

In accordance with the invention, site-specific mutagenesis can be carried out using PCT primers containing the desired modification. For example, as described in Examples 2-3, mutagenesis to produce a sequence encoding a CV-N variant having cysteine substituted for glutamine at position 62 (Gln62Cys) was accomplished using the QuikChange mutagenesis kit according to the manufacturer's protocol. The PCR primers used in the reaction had the following sequences, with the variant cysteine codon highlighted:

(SEQ ID NO: 10)
5'-CAACTCCGCTATCTGCGGTTCCGTTCTGACCTCC-3'

3'-GTTGAGGCGATAGACGCCAAGGCAAGACTGGAGG-5'

Similarly, a sequence encoding a CV-N variant having cysteine substituted for glutamine at position 14 (Glnl4Cys) was produced using the following primers, with the variant cysteine codon highlighted:

(SEQ ID NO: 11)
5'-CCTGCCGTAACACCTGCCTGGCTGGTTCCTCCG-3'

3'-GGACGGCATTGTGGACGGACCGACCAAGGAGGC-5'

Accordingly, polynucleotides encoding these variants, and optimized for expression in *E. coli*, would include the following sequences (SEQ ID NOs: 12 and 13), respectively:

preferably encode between 1 and about 50 amino acids, more preferably between about 5 and about 30 additional amino acids, and even more preferably between about 5 and about 20 amino acids.

Alternatively, the fusion may provide regulatory, enzymatic, cell signaling, or intercellular transport functions. For example, a sequence encoding a plastid transit peptide may be added to direct a fusion protein to the chloroplasts within seeds. Such fusion partners preferably encode between 1 and about 1000 additional amino acids, more preferably between about 5 and about 500 additional amino acids, and even more preferably between about 10 and about 250 amino acids.

In an alternative embodiment, the nucleic acid molecule comprises a nucleic acid sequence that is greater than 85% identical, and more preferably greater than 86, 87, 88, 89, 90, 91, 92, 93, 94, 95, 96, 97, 98, or 99% identical to a nucleic acid sequence encoding a modified cyanovirin-N protein of the invention, complements thereof, and fragments of any of these sequences.

The percent identity is preferably determined using the "Best Fit" or "Gap" program of the Sequence Analysis Software Package™ (Version 10; Genetics Computer Group, Inc., University of Wisconsin Biotechnology Center, Madison, Wis.). "Gap" utilizes the algorithm of Needleman

```
CTTGGTAAAT TCTCCCAGAC CTGCTACAAC TCCGCTATCC AGGGTTCCGT (SEQ ID NO: 12)

TCTGACCTCC ACCTGCGAAC GTACCAACGG TGGTTACAAC ACCTCCTCCA

TCGACCTGAA CTCCGTTATC GAAAACGTTG ACGGTTCCCT GAAATGGCAG

CCGTCCAACT TCATCGAAAC CTGCCGTAAC ACCTGCCTGG CTGGTTCCTC

CGAACTGGCT GCTGAATGCA AAACCCGTGC TCAGCAGTTC GTTTCCACCA

AAATCAACCT GGACGACCAC ATCGCTAACA TCGACGGTAC CCTGAAATAC

GAATAA

CTTGGTAAAT TCTCCCAGAC CTGCTACAAC TCCGCTATCT GCGGTTCCGT (SEQ ID NO: 13)

TCTGACCTCC ACCTGCGAAC GTACCAACGG TGGTTACAAC ACCTCCTCCA

TCGACCTGAA CTCCGTTATC GAAAACGTTG ACGGTTCCCT GAAATGGCAG

CCGTCCAACT TCATCGAAAC CTGCCGTAAC ACCCAGCTGG CTGGTTCCTC

CGAACTGGCT GCTGAATGCA AAACCCGTGC TCAGCAGTTC GTTTCCACCA

AAATCAACCT GGACGACCAC ATCGCTAACA TCGACGGTAC CCTGAAATAC

GAATAA
```

Any of the nucleic acid agents of the invention may be linked with additional nucleic acid sequences to encode fusion proteins. The additional nucleic acid sequence preferably encodes at least one amino acid, peptide, or protein. Many possible fusion combinations exist. For instance, the encoded fusion protein may provide a "tagged" epitope to facilitate detection of the fusion protein, such as GST, GFP, FLAG, or polyHIS. Such nucleic acid molecule fusions and Wunsch to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman. The percent identity calculations may also be performed using the Megalign program of the LASERGENE bioinformatics computing suite (default parameters, DNASTAR Inc., Madison, Wis.). The percent identity is most preferably determined using the "Best Fit" program using default parameters.

The present invention also provides nucleic acid molecule fragments that hybridize to the above-described nucleic acid molecules and complements thereof, fragments of nucleic acid molecules that exhibit greater than 80%, 85%, 90%, 95% or 99% sequence identity with the above-described nucleic acid molecules and complements thereof, or fragments of any of these molecules.

Nucleic acid hybridization is a technique well known to those of skill in the art of DNA manipulation. The hybridization properties of a given pair of nucleic acids are an indication of their similarity or identity. The nucleic acid molecules preferably hybridize, under low, moderate, or high stringency conditions, with a nucleic acid sequence encoding a cyanovirin-N protein variant of the invention, or a complement of such a nucleic acid sequence. Fragments of these sequences are also contemplated.

The hybridization conditions typically involve nucleic acid hybridization in about 0.1× to about 0.1×SSC (diluted from a 20×SSC stock solution containing 3 M sodium chloride and 0.3 M sodium citrate, pH 7.0 in distilled water), about 2.5× to about 5× Denhardt's solution (diluted from a 50× stock solution containing 1% (w/v) bovine serum albumin, 1% (w/v) Ficoll™, and 1% (w/v) polyvinylpyrrolidone in distilled water), about 10 mg/mL to about 100 mg/mL fish sperm DNA, and about 0.02% (w/v) to about 0.1% (w/v) SDS, with an incubation at about 20° C. to about 70° C. for several hours to overnight. The stringency conditions may be preferably provided by 6×SSC, 5× Denhardt's solution, 100 mg/mL fish sperm DNA, and 0.1% (w/v) SDS, with an incubation at 55° C. for several hours.

The hybridization is generally followed by several wash steps. The wash compositions generally comprise 0.1× to about 10×SSC, and 0.01% (w/v) to about 0.5% (w/v) SDS with a 15 minute incubation at about 20° C. to about 70° C. Preferably, the nucleic acid segments remain hybridized after washing at least one time in 0.1×SSC at 65° C. For example, the salt concentration in the wash step can be selected from a low stringency of about 2.0×SSC at 50° C. to a high stringency of about 0.2 ×SSC at 65° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

Low stringency conditions may be used to select nucleic acid sequences with lower sequence identities to a target nucleic acid sequence. One may wish to employ conditions such as about 6.0×SSC to about 10×SSC, at temperatures ranging from about 20° C. to about 55° C., and preferably a nucleic acid probe will hybridize to one or more of the above-described nucleic acid sequences under low stringency conditions of about 6.0×SSC and about 45° C. In a preferred embodiment, a nucleic acid probe will hybridize to one or more of the above-described nucleic acid sequences under moderately stringent conditions, for example at about 2.0×SSC and about 65° C. In a particularly preferred embodiment, a nucleic acid probe of the present invention will hybridize to one or more of the above-described nucleic acid sequences under high stringency conditions such as 0.2×SSC and about 65° C.

Fragment nucleic acid molecules may consist of significant portion(s) of, or indeed most of, the nucleic acid molecules of the invention. In an embodiment, the fragments are between about 300 and about 30 consecutive nucleotides, about 280 and about 50 consecutive nucleotides, about 250 and about 60 consecutive nucleotides, about 200 and about 80 consecutive nucleotides, about 150 and about 50 consecutive nucleotides, or between about 100 and about 25 consecutive nucleotides, or between about 50 and about 10 consecutive nucleotides long of a nucleic molecule of the present invention. In another embodiment, the fragment comprises at least 20, 30, 40, 50, 60, 70, 80, 90, 100, 150, 200, or 250 consecutive nucleotides of a nucleic acid sequence of the invention.

IV. Recombinant Vectors and Constructs

The invention also includes recombinant vectors or constructs comprising a nucleic acid molecule of the invention, or encoding a cyanovirin-N protein variant of the invention. The vectors and constructs of the invention can be used to transfer exogenous and/or heterologous genetic material into a host cell. The vector may be a linear or a closed circular plasmid. The vector system may be a single vector or plasmid or two or more vectors or plasmids that together contain the total DNA to be introduced into the genome of the host. Means for preparing recombinant vectors are well known in the art.

A. Vectors

A construct or vector may include a promoter; e.g., a recombinant vector typically comprises, in a 5' to 3' orientation, a promoter to direct the transcription of a nucleic acid sequence of interest, and a nucleic acid sequence of interest. Suitable promoters include, but are not limited to, those described herein. The recombinant vector may further comprise a 3' transcriptional terminator, a 3' polyadenylation signal, other untranslated nucleic acid sequences, transit and targeting nucleic acid sequences, selectable markers, enhancers, and operators, as desired.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. For autonomous replication, the vector may further comprise an origin of replication enabling the vector to replicate autonomously in the host cell in question. Alternatively, the vector may be one that, when introduced into the cell, is integrated into the genome and replicated together with the chromosome(s) into which it has been integrated. This integration may be the result of homologous or non-homologous recombination.

Integration of a vector or nucleic acid into the genome by homologous recombination, regardless of the host being considered, relies on the nucleic acid sequence of the vector. Typically, the vector contains nucleic acid sequences for directing integration by homologous recombination into the genome of the host. These nucleic acid sequences enable the vector to be integrated into the host cell genome at a precise location or locations in one or more chromosomes. To increase the likelihood of integration at a precise location, the vector preferably contains two nucleic acid sequences that individually contain a sufficient number of nucleic acids, preferably about 400 bp to about 1500 bp, more preferably about 800 bp to about 1000 bp, which are highly homologous with the corresponding host cell target sequence. These nucleic acid sequences may be any sequence that is homologous with a host cell target sequence and, furthermore, may or may not encode proteins.

Vectors suitable for replication in mammalian cells may include viral replicons, or sequences that ensure integration of the appropriate sequences encoding CV-N variant polypeptides into the host genome. For example, another vector used to express foreign DNA is vaccinia virus. Such heterologous DNA is generally inserted into a gene that is non-essential to the virus, for example, the thymidine kinase gene (tk), which also provides a selectable marker. Expression of the CV-N variant polypeptide then occurs in cells or animals that are infected with the live recombinant vaccinia virus.

In general, plasmid vectors containing replicon and control sequences that are derived from species compatible with the host cell are used in connection with bacterial hosts. The vector ordinarily carries a replication site, as well as marking sequences that are capable of providing phenotypic selection in transformed cells. For example, *E. coli* is typically transformed using pBR322, which contains genes for ampicillin and tetracycline resistance and thus provides easy means for identifying transformed cells. The pBR322 plasmid, or other microbial plasmid or phage, also generally contains, or is modified to contain, promoters that can be used by the microbial organism for expression of the selectable marker genes.

B. Promoters

Promoters used in the context of the invention are selected on the basis of the cell type into which the vector will be inserted. Promoters that function in bacteria, yeast, mammalian cells, and plants are all taught in the art. The promoters may also be selected on the basis of their regulatory features, e.g., enhancement of transcriptional activity, inducibility, tissue specificity, and developmental stage-specificity. Additional promoters that may be utilized are described, for example, in U.S. Pat. Nos. 5,378,619; 5,391,725; 5,428,147; 5,447,858; 5,608,144; 5,614,399; 5,633,441; 5,633,435; and 4,633,436.

For example, suitable promoters for mammalian cells are known in the art and include viral promoters, such as those from Simian Virus 40 (SV40), Rous sarcoma virus (RSV), adenovirus (ADV), cytomegalovirus (CMV), and bovine papilloma virus (BPV), as well as mammalian cell-derived promoters. Other preferred promoters include the hematopoietic stem cell-specific, e.g., CD34, glucose-6-phosphotase, interleukin-1 alpha, CD11c integrin gene, GM-CSF, interleukin-5R alpha, interleukin-2, c-fos, h-ras, and DMD gene promoters.

Inducible promoters suitable for use with bacteria hosts include the β-lactamase and lactose promoter systems, the arabinose promoter system, alkaline phosphatase, a tryptophan (trp) promoter system and hybrid promoters such as the tac promoter. However, other known bacterial inducible promoters are suitable. Promoters for use in bacterial systems also generally contain a Shine-Dalgarno sequence operably linked to the DNA encoding the polypeptide of interest.

Examples of suitable promoters for an algal host are light harvesting protein promoters obtained from photosynthetic organisms, *Chlorella* virus methyltransferase promoters, CaMV 35 S promoter, PL promoter from bacteriophage λ, nopaline synthase promoter from the Ti plasmid of *A. tumefaciens*, and bacterial trp promoter.

Vectors for use with insect cells or insects may utilize a baculovirus transcriptional promoter including, e.g., but not limited to the viral DNAs of *Autographa californica* MNPV, *Bombyx mori* NPV, *Trichoplusia ni* MNPV, *Rachiplusia ou* MNPV or *Galleria mellonella* MNPV, wherein the baculovirus transcriptional promoter is a baculovirus immediate-early gene IEI or IEN promoter; an immediate-early gene in combination with a baculovirus delayed-early gene promoter region selected from the group consisting of 39K and a HindIII-k fragment delayed-early gene; or a baculovirus late gene promoter.

C. Other Elements in the Recombinant Vector

Various cis-acting untranslated 5' and 3' regulatory sequences may be included in the recombinant nucleic acid vector to produce desirable regulatory features, such as transcriptional initiation and termination signals. The regulatory sequences may be provided by the DNA sequence encoding the cyanovirin-N protein variant of interest or a convenient transcription termination region derived from a different gene source.

Translational enhancers may also be incorporated as part of the recombinant vector, such as one or more 5' non-translated leader sequences that serve to enhance expression of the nucleic acid sequence. Such enhancer sequences may be desirable to increase or alter the translational efficiency of the resultant mRNA. Preferred 5' nucleic acid sequences include dSSU 5', PetHSP70 5', and GmHSP17.9 5'. Such sequences can be derived from the promoter selected to express the gene or can be specifically modified to increase translation of the mRNA. Such regions can also be obtained from viral RNAs, from suitable eukaryotic genes, or from a synthetic gene sequence. For a review of optimizing expression of transgenes, see Koziel et al., *Plant Mol. Biol.* 32:393-405 (1996).

The recombinant vector can further comprise a nucleic acid sequence encoding a transit peptide. This peptide may be useful for directing a protein to the extracellular space or to some other compartment inside or outside of the cell. (See, e.g., EP 0218571; U.S. Pat. Nos.: 4,940,835, 5,610,041, 5,618,988, and 6,107,060).

The nucleic acid sequence in the recombinant vector may comprise introns. The introns may be heterologous with respect to the structural nucleic acid sequence.

A nucleic acid molecule of the invention may also be operably linked to a suitable leader sequence. A leader sequence is a nontranslated region of a mRNA that is important for translation by the host. The leader sequence is operably linked to the 5' terminus of the nucleic acid sequence encoding the protein or fragment thereof A poly-adenylation sequence may also be operably linked to the 3' terminus of the nucleic acid sequence of the invention. The polyadenylation sequence is a sequence that when transcribed is recognized by the host to add polyadenosine residues to transcribed mRNA.

A nucleic acid molecule of the invention may also be linked to a propeptide coding region. A propeptide is an amino acid sequence found at the amino terminus of a proprotein or proenzyme. Cleavage of the propeptide from the proprotein yields a mature biochemically active protein. Propolypeptides are generally inactive and can be converted to mature active polypeptides by catalytic or autocatalytic cleavage of the propeptide from the propolypeptide or proenzyme.

The recombinant vectors can further comprise one or more sequences that encode one or more factors that are advantageous in the expression of the protein or peptide, for example, an activator (e.g., a trans-acting factor), a chaperone and a processing protease. An activator is a protein that activates transcription of a nucleic acid sequence encoding a polypeptide, a chaperone is a protein that assists another protein in folding properly, and a processing protease is a protease that cleaves a propeptide to generate a mature biochemically active polypeptide. The nucleic acids encoding one or more of these factors are preferably not operably linked to the nucleic acid encoding the protein or fragment thereof.

V. Transgenic Organisms

One or more of the nucleic acid molecules or recombinant vectors of the invention may be used to transform a host cell or organism. The invention is also directed to transformed host cells that comprise, in a 5' to 3' orientation, a promoter operably linked to a heterologous nucleic acid molecule of the invention, or encoding a cyanovirin-N protein variant of the invention. Additional nucleic acid sequences may be introduced into the host cell, such as 3' transcriptional terminators, 3' polyadenylation signals, other untranslated nucleic acid sequences, transit or targeting sequences, selectable markers, enhancers, and operators. Preferred nucleic acid sequences of the present invention, including recombinant vectors, structural nucleic acid sequences, promoters, and other regulatory elements, are described above.

Another embodiment of the invention is directed to a method of producing such transformed host cells, which generally comprises the steps of selecting a suitable host cell, transforming the host cell with a recombinant vector, and obtaining the transformed host cell.

A transformed host cell may generally be any cell which is compatible with the present invention. A transformed host cell can be or derived from a plant, or from a cell or organism such as a mammalian cell, mammal, fish cell, fish, bird cell, bird, algae cell, algae, fungal cell, fungus, or bacterial cell. Preferred host and transformants include: fungal cells such as *Aspergillus*, yeasts, mammals, particularly bovine and porcine, insects, bacteria, and algae. Methods to transform such cells or organisms are known in the art. See, e.g., EP 238023; Becker and Guarente, in: Abelson and Simon (eds.), *Guide to Yeast Genetics and Molecular Biology, Methods Enzymol*. 194:182-187, Academic Press, Inc., New York; Bennett and LaSure (eds.), *More Gene Manipulations in Fungi*, Academic Press, CA. (1991); Hinnen et al., *PNAS* 75:1920 (1978); Ito et al., *J. Bacteriology* 153:163 (1983); Malardier et al, *Gene* 78:147-156 (1989); Yelton et al., *PNAS* 81:1470-1474 (1984).

Mammalian cell lines available as hosts for expression are known in the art and include many immortalized cell lines available from the American Type Culture Collection (ATCC, Manassas, Va.), such as HeLa cells, Chinese hamster ovary (CHO) cells, baby hamster kidney (BHK) cells and a number of other cell lines.

The fungal host cell may, for example, be a yeast cell, a fungi, or a filamentous fungal cell. In one embodiment, the fungal host cell is a yeast cell, and in a preferred embodiment, the yeast host cell is a cell of the species of *Candida, Kluyveromyces, Saccharomyces, Schizosaccharomyces, Pichia* and *Yarrowia*. In another embodiment, the fungal host cell is a filamentous fungal cell, and in a preferred embodiment, the filamentous fungal host cell is a cell of the species of *Acremonium, Aspergillus, Fusarium, Humicola, Myceliophthora, Mucor, Neurospora, Penicillium, Thielavia, Tolypocladium* and *Trichoderma*.

Suitable host bacteria include archaebacteria and eubacteria, especially eubacteria and most preferably *Enterobacteriaceae*. Examples of useful bacteria include *Escherichia, Enterobacter, Azotobacter, Erwinia, Bacillus, Pseudomonas, Klebsiella, Proteus, Salmonella, Serratia, Shigella, Rhizobia, Vitreoscilla* and *Paracoccus*. Suitable *E. coli* hosts include *E. coli* W3110 (ATCC 27325), *E. coli* 294 (ATCC 31446), *E coli* B and *E. coli* X1776 (ATCC 31537) (American Type Culture Collection, Manassas, Va.). Mutant cells of any of the above-mentioned bacteria may also be employed. These hosts may be used with bacterial expression vectors such as *E. coli* cloning and expression vector Bluescript™ (Stratagene, La Jolla, Calif.); pIN vectors (Van Heeke and Schuster 1989), and pGEX vectors (Promega, Madison Wis.), which may be used to express foreign polypeptides as fusion proteins with glutathione S-transferase (GST).

Preferred insect host cells are derived from *Lepidopteran* insects such as *Spodoptera frugiperda* or *Trichoplusia ni*. The preferred *Spodoptera frugiperda* cell line is the cell line Sf9 (ATCC CRL 1711). Other insect cell systems, such as the silkworm *B. mori* can also be used. These host cells are preferably used in combination with Baculovirus expression vectors (BEVs), which are recombinant insect viruses in which the coding sequence for a chosen foreign gene has been inserted behind a baculovirus promoter in place of the viral gene, e.g., polyhedrin (U.S. Pat. No. 4,745,051).

Technology for introduction of nucleic acids into cells is well known to those of skill in the art. Common methods include chemical methods, microinjection, electroporation (U.S. Pat. No. 5,384,253), particle acceleration, viral vectors, and receptor-mediated mechanisms. Fungal cells may be transformed by a process involving protoplast formation, transformation of the protoplasts and regeneration of the cell wall. The various techniques for transforming mammalian cells are also well known.

Algal cells may be transformed by a variety of known techniques, including but not limit to, microprojectile bombardment, protoplast fusion, electroporation, microinjection, and vigorous agitation in the presence of glass beads. Suitable procedures for transformation of green algal host cells are described in EP 108580. A suitable method of transforming cells of diatom *Phaeodactylum tricornutum* species is described in WO 97/39106. Chlorophyll C-containing algae may be transformed using the procedures described in U.S. Pat. No. 5,661,017.

Methods for introducing nucleic acids into plants are also well known. Suitable methods include bacterial infection (e.g., *Agrobacterium*), binary bacterial artificial chromosome vectors, direct delivery of nucleic acids (e.g., via PEG-mediated transformation), desiccation/inhibition-mediated nucleic acid uptake, electroporation, agitation with silicon carbide fibers, and acceleration of nucleic acid coated particles, etc. (reviewed in Potrykus et al, *Ann. Rev. Plant Physiol. Plant Mol. Biol.* 42:205, 1991). For example, electroporation has been used to transform maize protoplasts.

Transfer of a nucleic acid that encodes a cyanovirin-N protein variant of the invention can result in expression or overexpression of that protein in a transformed cell or transgenic organism. Such expression or overexpression may be the result of transient or stable transfer of the exogenous genetic material.

The expressed protein may be detected using methods known in the art that are specific for the particular protein or fragment. These detection methods may include the use of specific antibodies, formation of an enzyme product, or disappearance of an enzyme substrate. For example, if the protein has enzymatic activity, an enzyme assay may be used. Alternatively, if polyclonal or monoclonal antibodies specific to the protein are available, immunoassays may be employed using the antibodies to the protein. The techniques of enzyme assay and immunoassay are well known to those skilled in the art.

The resulting protein may be recovered by methods known in the arts. For example, the protein may be recovered from the nutrient medium by procedures including, but not limited to, centrifugation, filtration, extraction, spray-drying, evaporation, or precipitation. The recovered protein may then be further purified by a variety of chromatographic procedures, e.g., ion exchange chromatography, gel filtration chromatography, affinity chromatography, or the like. Reverse-phase high performance liquid chromatography (RP-HPLC), optionally employing hydrophobic RP-HPLC media, e.g., silica gel, further purify the protein. Combinations of methods and means can also be employed to provide a substantially purified recombinant polypeptide or protein.

VI. Protein-Polymer Conjugates

In accordance with the invention, protein-polymer conjugates are provided wherein a cyanovirin-N protein variant, as described above, is coupled to at least one water-soluble polymer. Preferably, the variant includes one to four cysteine substitutions or insertions at a position selected from 9-21, 29-40, 45-49, 57, 59-72, 79-91, and 96-101 of SEQ ID NO: 1, more preferably from positions 10-20, 31-39, 46-48, 60-71, 80-90, and 97-100, and most preferably from positions 14 and 62 (Gln residues), 11, 16, 20, 32, 33,38, 46, 67, 68, and 82 (Ser residues), and 19, 21, 31, 57, 61, and 83 (Thr residues). In selected embodiments, the variant includes one or two such substitutions. Alternatively, the nucleic acid molecule may encode a variant in which all or all but one of the lysine residues of SEQ ID NO: 1 is converted to asparagine. As noted above, such variants are useful for site-specific attachment of water soluble polymers, to produce therapeutically useful CV-N-polymer conjugates.

The conjugate may also include, linked to a water soluble polymer, a fragment corresponding to, or having at least 70% sequence homology to, a portion of SEQ ID NO: 1, where the fragment contains at least one modified site for attachment of a polymer, as described above. The fragment is one that retains measurable degree of cyanovirin antiviral activity (e.g., from at least about 15% to about 100% or more of the biological activity of native CV-N). Preferably, the fragment includes at least nine amino acids, more preferably at least twenty, and most preferably at least forty amino acids. In one embodiment, the fragment includes a sequence corresponding to residues 40-80 of SEQ ID NO: 1, incorporating one or more of the preferred amino acid substitutions or insertions described herein.

Examples of suitable water soluble polymers to be attached to the variant protein include, but are not limited to, poly(alkylene glycols) such as polyethylene glycol (PEG), poly(propylene glycol) ("PPG"), copolymers of ethylene glycol and propylene glycol and the like, poly(oxyethylated polyol), poly(olefinic alcohol), poly(vinylpyrrolidone), poly (α-hydroxyalkylmethacrylamide), poly(hydroxyalkylmethacrylate), poly(saccharides), poly (α-hydroxy acid), poly(vinyl alcohol), polyphosphazene, polyoxazoline, poly (N-acryloylmorpholine), and copolymers, terpolymers, and mixtures thereof.

In a preferred embodiment, the cyanovirin-N protein variant is coupled to a poly(alkylene oxide) polymer such as PEG. The PEG is preferably coupled at a cysteine residue which has been added via substitution or addition, as described above.

Preferably, the protein-polymer conjugates of the invention maintain at least a measurable degree of specific activity. That is to say, a protein-polymer conjugate in accordance with the invention will possesses anywhere from about 15% to about 100% or more of the specific activity of native cyanovirin-N. In one preferred embodiment of the invention, the protein-polymer conjugate of the invention will possess at least 20% or more of the biological activity of unmodified, native cyanovirin-N. Preferably, the bioactivity of a conjugate will be at least about 30%, preferably at least about 40%, more preferably at least about 50% and even more preferably at least about 60% or more of the bioactivity of native cyanovirin-N.

Bioactivity typically decreases with increased molecular weight of the attached protein. As discussed below, a combination of bioactivity and enhanced pharmacokinetics may be achieved by. preparing a protein-polymer conjugate having a high molecular weight polymer component and an in vivo cleavable linkage. In this case, the uncleaved conjugate may have a low level of bioactivity. Such linkages may include, for example, ester, carbamate, carbonate, sulfate, acyloxyalkyl ether, imine, phosphate ester, hydrazone, acetal, ketal, or orthoester linkages. In this case, substitution at or near an active or binding site of the protein may be feasible, since cleavage of the polymer regenerates the active site or a structurally similar site, particularly when the amino acid substitution is a conservative substitution, as described above. Preferably, a cleavage mechanism is employed which regenerates the linking amino acid in its native form or in a minimally altered form. See, for example, U.S. Pat. No. 6,413,507.

The bioactivity of an antiviral conjugate in accordance with the invention may be characterized using an antiviral assay such as those described in Examples 5 and 6 or by RIA (radioimmunoassay). A suitable assay for assessing anti-HIV activity of a variant or conjugate of the invention is described in Boyd, M., "Strategies for the Identification of New Agents for the Treatment of AIDS: A National Program to Facilitate the Discovery and Preclinical Development of New Drug Candidates for Clinical Evaluation", *AIDS Etiology, Diagnosis, Treatment, and Prevention*, 2$^{nd}$ Edition, De Vita et al., eds, J. B. Lippincott and Co., 1988, pp. 305-317; and in Weislow et al., *J. Natl. Cancer Inst.*, 81, 577-586 (1989).

A. The Water Soluble Polymer

A1. Backbone Composition

Any of a variety of monofunctional, bifunctional or multifunctional polymers that are non-peptidic and water-soluble can be used to form a CV-N variant conjugate in accordance with the present invention. Such polymers include, for example, homopolymers or copolymers of one or more monomers selected from alkylene glycols, olefinic alcohols, vinyl pyrrolidone, hydroxyalkyl methacrylamides, hydroxyalkyl methacrylates, saccharides, α-hydroxy acids, phosphazene, oxazoline, and N-acryloylmorpholine.

In a preferred embodiment, the polymer is a poly(alkyene oxide) polymer. Poly(alkylene oxide) based polymer backbones that are water-soluble, with from 1 to about 300 termini, are particularly useful in the invention. Examples of suitable polymers include, but are not limited to, other poly(alkylene glycols), such as poly(propylene glycol) ("PPG"), copolymers thereof (e.g. copolymers of ethylene glycol and propylene glycol), terpolymers thereof, mixtures thereof, and the like. Although the molecular weight of each chain of the polymer backbone can vary, it is typically in the range of from about 800 Da to about 100,000 Da, often from about 6,000 Da to about 80,000 Da.

A preferred poly(alkylene oxide) backbone useful in the invention is poly(ethylene glycol) (i.e. PEG). However, it should be understood that other related polymers are also suitable for use in the practice of this invention and that the use of the term PEG or poly(ethylene glycol) is intended to be inclusive and not exclusive in this respect. The term PEG includes poly(ethylene glycol) in any of its forms, including linear PEG, multi-armed PEG, forked PEG, branched PEG, pendant PEG (i.e. PEG or related polymers having one or more functional groups pendant to the polymer backbone), or PEG with degradable linkages therein, to be described in greater detail, below.

PEG having the formula —$CH_2CH_2O$—$(CH_2CH_2O)_n$—$CH_2CH_2$—, where n is from about 3 to about 4000, typically from about 20 to about 2000, is an exemplary polymer in the practice of the invention. Typically, a PEG polymer for use in forming a conjugate of the invention will possess a molecular weight of from about 350 Da to about 200,000 Da. Typically, the number average molecular weight of the polymer portion of a polymer conjugate of the invention is from about 100 daltons (Da) to about 100,000 Da, preferably about 500 daltons to about 100,000 daltons. Even more preferably, PEGs for use in the invention will have a molecular weight from about 350 daltons to about 40,000 daltons. Representative PEG moieties for covalent attachment to a cyanovirin variant may possess any one of the following average molecular weights: 750 daltons, 1000 daltons, 5000 daltons, 7500 daltons, 10,000 daltons, 15,000 daltons, 20,000 daltons, 25,000 daltons, 30,000 daltons, 35,000 daltons, or about 40,000 daltons.

One particularly preferred polymer for use in the invention is an end-capped polymer, meaning a polymer having at least one terminus capped with a relatively inert group, such as a lower C1-C6 alkoxy group. One such particularly preferred form of PEG is methoxy-PEG (commonly referred to as mPEG), a linear form of PEG wherein one terminus of the polymer is a methoxy (—OMe) group. The other terminus is a hydroxyl or other functional group that can be chemically modified for conjugation with a CV-N variant of the invention, as described below.

The polymers may also include one or more weak or degradable linkages in the polymer backbone, as discussed further below.

A2. Functional Groups

Poly(alkylene oxide) polymers useful in the present invention include poly(alkylene oxide) polymers that are activated at at least one terminus with a functional group effective to selectively react at a desired position on the CV-N variant protein. In one embodiment, the functional group is selective for reaction with thiol groups (ie., a sulfhydryl-selective moiety), such as those present in cysteine. Any such sulfhydryl-selective functional group known in the art may be used. PEG derivatives having at least one reactive terminus that is a maleimide, vinylsulfone, thiol, iodoacetamide, or orthopyridyl disulfide, are reagents that are suitable for PEGylation of cysteine residues, such as those contained in the CV-N variants of the invention. See, for example, such derivative as described in U.S. Pat. Nos. 5,739,208 and 6,602,498 and International Patent Publication No. WO 01/62827. Exemplary sulfhydryl-selective PEGs for use in this particular embodiment of the invention include those described above, e.g., mPEG-forked maleimide (mPEG(MAL)$_2$), mPEG2-forked maleimide (mPEG2 (MAL)$_2$), mPEG-maleimide (mPEG-MAL), and mPEG2-maleimide (mPEG2-MAL) (Shearwater Corporation). The structures of these activated PEGs are as follows: mPEG-CONHCH[CH$_2$CONH(CH$_2$CH$_2$O)$_2$CH$_2$CH$_2$-MAL, mPEG2-lysine-NH—CH [CH$_2$CONH(CH$_2$CH$_2$O)$_2$CH$_2$CH$_2$-MAL]$_2$, MPEG-MAL, and mPEG2-lysine-NH—CH$_2$CH$_2$NHC(O)CH$_2$CH$_2$MAL, respectively.

Alternatively, amine-reactive reagents may be used, when the CV-N variant is modified to provide selective reaction with such a reagent (i.e. by conversion or all or all but one Lys residue to Arg, for reaction at a specific Lys and/or the N-terminus). Such reagents include, for example, NHS esters (U.S. Pat. No. 6,214,966) such as mPEG-succinimidyl propionic acid (SPA), benzotriazole carbonates (U.S. Pat. No. 6,376,604), acetals and aldehydes (U.S. Pat. No. 5,990, 237), e.g mPEG-propionaldehyde.

Particularly preferred functionalized PEGs include linear MPEG having a sulthydryl selective reactive group at the reactive terminus, or a bifunctional linear or dumbbell-type PEG having reactive termini at both ends, where the reactive groups may be the same or different. Preferably the reactive groups are thiol-specific or thiol-selective.

One PEG derivative falling into this category is mPEG-MAL, depicted below. This polymer derivative is a linear, end-capped PEG having a terminus selective for coupling to thiol groups. In one embodiment of the invention, the polymer for coupling to a CV-N variant is an niPEG-MAL having no linking group between the terminus of the polymer and the nitrogen atom of the MAL moiety. Polymers of this sort are particularly preferred for use in coupling to a CV-N variant of the invention and are described in International Patent Publication No. WO 01/62827 (Shearwater Corporation).

mPEG-MAL

The coupling reaction using the PEG derivative above proceeds as shown below, where "HS" represents a thiol or sulfhydryl group on a cysteine substituted or inserted into a CV-N variant of the invention:

mPEG-N + HS$_{cys}$—CV—N$_{variant}$ → mPEG-N—S$_{cys}$—CV—N$_{variant}$

Alternatively, the polymer backbone may be covalently attached to the nitrogen atom of a maleimide ring through a linker. The linker typically includes a saturated acyclic or alicyclic hydrocarbon chain adjacent to the nitrogen of the maleimide ring, as described in U.S. Provisional Patent Application Ser. No. 60/437,211. The hydrocarbon chain has a chain length of up to about 20 carbon atoms, and may comprise alkylene chains, bivalent cycloalkyl groups, or combinations thereof. The linker may also include a hydrolytically stable linkage, e.g. a carbamate linkage, adjacent to the polymer backbone.

The saturated acyclic or alicyclic hydrocarbon portion of the linker adjacent to the maleimide preferably has a chain length of at least 3 carbon atoms, more preferably at least about 4 carbon atoms, most preferably at least about 5 carbon atoms. One- and two-carbon chains are also included. The chain length is measured as the number of carbon atoms forming the shortest atom chain linking the nitrogen atom of the maleimide to the non-hydrocarbon portion of the linkage, if present, or to the polymer backbone. The chain length can include an acyclic hydrocarbon chain, a saturated alicyclic hydrocarbon, or a combination thereof, depending on the structure of the linkage. Typically, the total number of carbon atoms in the hydrocarbon portion of the linkage, including chain substituents, ranges from 4 to about 20 atoms, preferably 4 to about 12 atoms, more preferably 4 to about 10 atoms and most preferably 5 to about 8 atoms. The invention includes hydrocarbon linkages having, for example, 4, 5, 6, 7, 8, 9, 10, 11, and 12 total carbon atoms.

Exemplary linkages including a hydrocarbon chain according to the present invention are shown in Table 3 below.

TABLE 3

POLY—L—N (maleimide)

1: L = —NH—C(=O)—X—

AMPE; X = pentamethylene

MCH; X = —(cyclohexyl)—CH$_2$—

TEPE; X = —CH$_2$—[O—CH$_2$CH$_2$]$_4$—O—C(=O)—NH—CH$_2$CH$_2$—CH(CH$_3$)—CH$_2$—

2: L = —NH—Y—
TEME; Y = tetramethylene
HEXA; Y = hexamethylene

EPEN; Y = —CH$_2$CH$_2$—CH(CH$_3$)—CH$_2$—CH$_2$—

3: L = —O—Z—
TEME; Z = tetramethylene
PENT; Z = pentamethylene
HEXA; Z = hexamethylene

4: L = —CH$_2$—Z—

PAHE; Z = —C(O)NH-hexamethylene
BAHE; Z = methylene-C(O)NH-hexamethylene

TMPA; Z = —C(O)NH—C(CH$_3$)$_2$—CH$_2$—C(CH$_3$)$_2$—

TABLE 3-continued

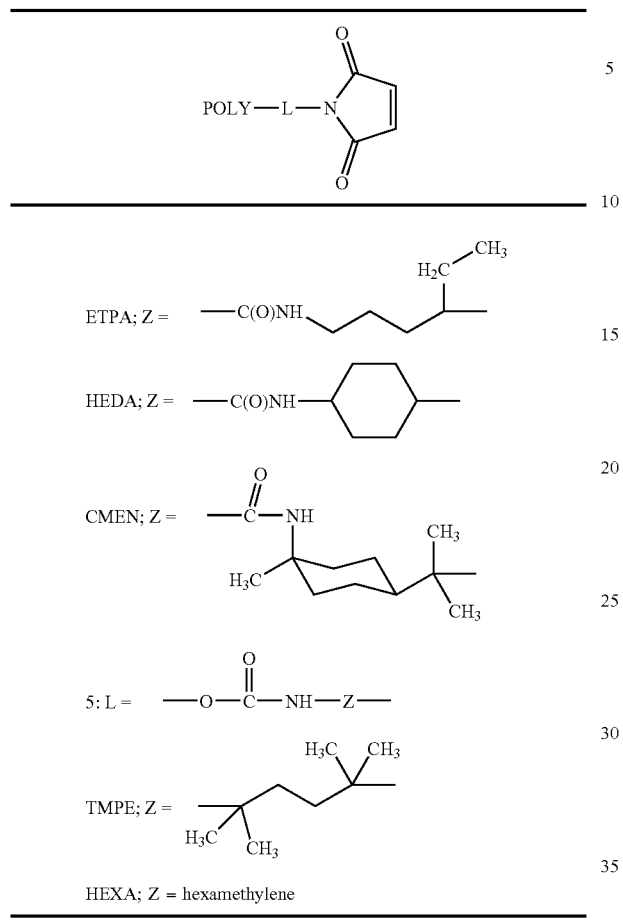

ETPA; Z =

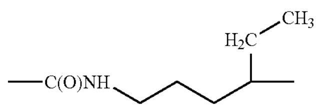

HEDA; Z =

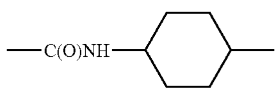

CMEN; Z =

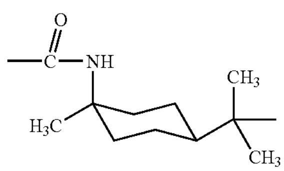

5: L =

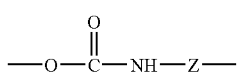

TMPE; Z =

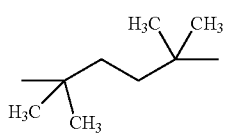

HEXA; Z = hexamethylene

A3. Polymer Structural Variations

The conjugates of the invention may employ linear polymers, such as linear mPEGs. Alternatively, multi-armed or branched polymers, such as PEG polymers described in U.S. Pat. No. 5,932,462, which is incorporated by reference herein, can be used to form a conjugate of the invention.

In one embodiment of the invention, the polymer derivatives are "multi-functional", meaning that the polymer backbone has at least three termini, and possibly as many as about 300 termini, functionalized or activated with a functional group such as maleimide.

Generally speaking, a multi-armed or branched polymer possesses two or more polymer "arms" extending from a central branch point or core moiety (e.g., C in the structure below) that is covalently attached, either directly or indirectly via intervening connecting atoms, to one active moiety, such as a CV-N variant. For example, an exemplary branched PEG polymer has the structure:

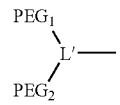

wherein $PEG_1$, and $PEG_2$ are PEG polymers in any of the forms or geometries described herein, and which can be the same or different, and L' is a hydrolytically stable linkage.

Such polymers may have 2 polymer arms, 3 polymer arms, 4-8 polymer arms, or even a plurality of polymer arms. Branched PEGs such as these can be prepared by addition of ethylene oxide to various polyols, such as glycerol, glycerol oligomers, pentaerythritol and sorbitol. The central branch moiety can also be derived from several amino acids, such as lysine. The branched poly(ethylene glycol) can be represented in general form as $R(\text{-PEG—OH})_m$ in which R is derived from a core moiety, such as glycerol, glycerol oligomers, or pentaerythritol, and m represents the number of arms.

For example, an exemplary branched PEG polymer falling under the general structure above may comprise the following structure:

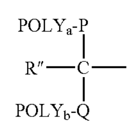

wherein: $POLY_a$ and $POLY_b$ are PEG polymers, such as methoxy poly(ethylene glycol); R" is a nonreactive moiety, such as H, methyl or PEG; and P and Q are nonreactive linkages. In a preferred embodiment, the branched PEG polymer comprising the above structural features is methoxy poly(ethylene glycol) disubstituted lysine or a derivative thereof. Illustrative branched PEG polymers for coupling to a CV-N variant of the invention include those available from Nektar, AL. Two illustrative polymers having a disubstituted lysine core are the forked mPEG2(MAL)2 and mPEG2MAL, whose structures are shown below.

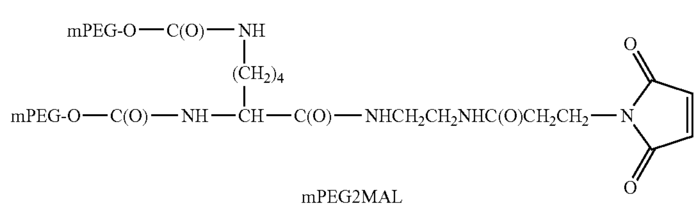

mPEG2MAL

-continued mPEG-O—C(O)—NH—CH—C(O)—NH—CH with (CH2)4 branch to mPEG-O—C(O)—NH, and CH bearing two CH2CONH(CH2CH2O)2—CH2CH2N(maleimide) groups mPEG2(MAL)2

As discussed previously, the polymer may alternatively have a forked structure such as that of mPEG2(MAL)2 above. Generally speaking, a polymer having a forked structure is characterized as having a polymer chain attached to two or more reactive groups via covalent linkages extending from a hydrolytically stable branch point in the polymer (see e.g. U.S. Pat. No. 6,362,254, which is incorporated herein by reference). Such a polymer can be used to effectively link two protein molecules to a single PEG molecule; i.e. $R^1$—S-PEG-S—$R^2$, where $R^1$ and $R^2$ may represent the same or different proteins, and S represents the thio group of a cysteine either present in the native protein or introduced by site-directed mutagenesis.

In the representative mPEG2(MAL)2 structure shown above, the central CH attached to the amido nitrogen of lysine is considered as a hydrolytically stable branch point. An example of a forked PEG is represented by PEG-Y-CHZ$_2$, where Y is a linking group and Z is an activated terminal group for covalent attachment to a biologically active agent, such as a CV-N variant. The Z group is linked to CH by a chain of atoms of defined length. International Application Pubn. No. WO 99/45964, the contents of which are incorporated by reference herein, describes various forked PEG structures suitable for use in the present invention. The chain of atoms linking the Z functional groups to the branching carbon atom serve as a tethering group and may comprise, for example, an alkyl or alkenyl chain, ether linkage, ester linkage, amide linkage, or combinations thereof. Preferred Z linking groups for use in coupling a forked PEG to a CV-N variant of the invention include maleimide, thiol, vinyl sulfone, iodoacetamide, or orthopyridyl disulfide.

A PEG polymer may also take the form of a pendant PEG molecule having reactive groups, such as hydroxyl, or more preferably maleimide, thiol, vinyl sulfone, iodoacetamide, or orthopyridyl disulfide, covalently attached along the length of the PEG backbone rather than at the ends of the PEG chain. Such pendant reactive groups may be attached to the PEG backbone directly or through a linking moiety, such as an alkyl or alkenyl chain.

Preferred polymers for use in preparing a cysteine-variant conjugate of the invention will possess any of the aforementioned representative geometries, with one or more termini suitable for coupling to a thiol group such as that contained in a cysteine. Illustrative coupling reactions and the resulting conjugates are shown below, where L is an optional spacer or linker group positioned between the PEG or other hydrophilic polymer backbone and the sulfhydryl-specific reactive group at the polymer terminus.

POLY-$L_{0,1}$—N(maleimide) + $HS_{cys}$—CV—$N_{variant}$ →

POLY-$L_{0,1}$—N(succinimide)—$S_{cys}$—CV—$N_{variant}$

POLY-$L_{0,1}$—NHC(O)CH$_2$I + $HS_{cys}$—CV—$N_{variant}$ →
POLY-$L_{0,1}$—NHC(O)CH$_2S_{cys}$—CV—$N_{variant}$ POLY-$L_{0,1}$—S(O)$_2$—CH=CH$_2$ + $HS_{cys}$—CV—$N_{variant}$ →
POLY-$L_{0,1}$—S(O)$_2$—CH$_2$CH$_2S_{cys}$—CV—$N_{variant}$ POLY-$L_{0,1}$—S—S—(2-pyridyl) + $HS_{cys}$—CV—$N_{variant}$ →
POLY-$L_{0,1}$—S—$S_{cys}$—CV—$N_{variant}$ B. Structure of the Protein-Polymer Conjugate A protein-polymer conjugate of the invention will typically comprise one or more poly(alkylene oxide) chains, preferably PEG chains, each having a molecular weight ranging from about 200 to about 40,000 daltons. While lower molecular weight PEGs may be preferred for increasing bioavailability, high molecular weight PEG chains, e.g., having an average molecular weight of 5,000, 10,000, 15,000, 20,000, 25,000, 30,000 or 40,000 daltons or greater may be preferred for increasing half-life, particularly in the case of injectable formulations. That is to say, a significant improvement in the pharmacokinetic parameters, e.g., the area under the curve (AUC), for a high molecular weight protein-polymer conjugate (relative to native), can more than compensate for its diminished activity.

Preferably, the PEGylated proteins have a half-life ($ti_2$) which is enhanced relative to the half-life of the unmodified protein from which it was derived. Preferably, the half-life of the cysteine-PEGylated protein is enhanced by at least 1.5-fold to 2-fold, more preferably by about 2-fold to 3-fold, even more preferably by about 5-fold to 10-fold, optimally about 100-fold, usually about 6-fold relative to the half-life of the unmodified parent protein.

The number and total molecular weight of PEG molecules covalently bound per protein may vary depending upon the desired protein stability (e.g. serum half-life). For relatively small proteins such as CV-N, which generally have short half-lives, it may be desirable to PEGylate the protein so as to increase the protein's total molecular weight to 30,000-40,000 MW or more. As described below (Example 9), PEGylation of CV-N with 30 kDa PEG gave superior pharmacological properties, even though the bioactivity was less than a conjugate employing 20 kDa PEG.

The number of polymers per protein is typically one to four, corresponding, for example, to the number of preferred cysteine substitutions in a variant protein, as described above. In selected embodiments, the conjugate includes one or two attached polymers per protein. The location of an attached polymer is determined by the location of the variant cysteine moiety. Alternatively, a polymer is attached to a lysine residue in a variant in which all of the other lysines have been substituted with arginine. The polymer may also be attached to a terminus of the protein. In general, the modifications carried out to produce the variant protein provide for site-specific, rather than random, attachment of polymers.

In another embodiment of the invention, the protein-polymer conjugate comprises two cyanovirin-N protein variants interconnected by a central PEG. More specifically, such conjugates may be represented by the structure protein-Y-PEG-Z-protein, where Y and Z are hydrolytically stable linking groups linking the cyanovirin-N protein variant to the PEG moiety. In a particular embodiment, the linkages Y and Z are formed by reaction of an activated sulfone or maleimide reagents with a thiol group on a cyanovirin-N protein variant.

The coupling of the poly(alkylene oxide) based polymer and the cyanovirin-N protein variant of the invention can be accomplished via any covalent attachment known in the art, including amide, secondary amine, ester, disulfide, ether, thioether, urea, carbamate, or any of the linkages shown above, depending of course upon the site(s) of attachment in the CV-N variant. In an alternative embodiment, in any of the representative structures provided herein, the chemical linkage between a cyanovirin-N protein variant and the polymer branch point may be degradable (i.e., hydrolytically unstable).

The conjugated polymer, including any of the above described polymers, can also include one or more weak or degradable linkages in the polymer backbone. That is to say, in addition to the linkage coupling the polymer to the CV-N variant, the polymer may contain additional hydrolyzable or otherwise degradable bonds within the polymer to provide further degradation of the polymer, thus providing in vivo generation of a protein-polymer conjugate having a smaller poly(alkylene oxide) chain than in the initially administered CV-N conjugate.

For example, a PEG can be prepared having ester linkages in the polymer backbone that are subject to hydrolysis. As shown below, this hydrolysis results in cleavage of the polymer into fragments of lower molecular weight:

$$\text{-PEG-CO}_2\text{-PEG-} + \text{H}_2\text{O} \longrightarrow \text{-PEG-CO}_2\text{H} + \text{HO-PEG-}$$

Other hydrolytically degradable linkages that may be contained within the polymer backbone include carbamate, carbonate, sulfate, and acyloxyalkyl ether linkages; imine linkages, resulting, for example, from reaction of an amine and an aldehyde (see, e.g., Ouchi et al., *Polymer Preprints*, 38(1):582-3 (1997), which is incorporated herein by reference); carbamate, phosphate ester, hydrazone, acetal, ketal, or orthoester linkages. Such physiologically cleavable bonds should be upon storage and upon administration. For instance, a protein-cleavable linkage-polymer conjugate should maintain its integrity upon manufacturing of the final pharmaceutical composition, upon dissolution in an appropriate delivery vehicle, if employed, and upon administration irrespective of route.

More particularly, as described generally above, protein-polymer conjugates having biodegradable linkages and useful in the present invention can be represented by the following structures: PEG1-W-PEG2-cyanovirin variant (where PEG1 and PEG2 can be the same or different) or PEG-W-cyanovirin variant, wherein W represents a linkage that is degradable in vivo.

The cleavable protein-polymer conjugates of the invention described above may be substantially biologically inactive when intact, either due to the size of the intact PEG portion of the molecule or due to steric blockage of the active sites on the cyanovirin-N protein variant by the PEG chain. However, such conjugates are cleaved under physiological conditions to thereby release the cyanovirin-N protein variant or a biologically active protein-polymer conjugate capable of absorption into the systemic circulation.

For example, a large and relatively inert conjugate (i.e., having one or more high molecular weight PEG chains attached thereto, e.g., one or more PEG chains having a molecular weight greater than about 10,000) may be administered, which then is hydrolyzed in vivo to generate a bioactive conjugate possessing a portion of the originally present PEG chain. In this way, the properties of the protein-polymer conjugate may be somewhat more effectively tailored. For instance, absorption of the initial polymer conjugate may be slow upon initial administration, e.g. by inhalation. Upon in vivo cleavage of the hydrolytically degradable linkage, either free cyanovirin-N protein variant (depending upon the position of the degradable linkage) or cyanovirin-N protein variant having a small polyethylene tag attached thereto, is then released and more readily absorbed through the lung and/or circulated in the blood.

In a first exemplary structure, the PEG1 portion may possess any of a number of different architectures discussed herein, and will typically possess a molecular weight of at least about 10,000, such that the conjugate is not rapidly absorbed upon administration. The PEG2 portion of the molecule preferably possesses a molecular weight of less than about 5000 daltons, more preferably less than 2000 daltons, and even more preferably less than 1000 daltons. Referring now to the secondary exemplary structure, PEG-W-protein, the PEG portion will generally possess a molecular weight of at least about 10,000 Daltons or more.

C. Preparation of the Protein-Polymer Conjugate

Water soluble polymers having functional groups for attachment to reactive groups on polypeptides, particularly to amine or thiol groups, are described above in Section A2. The reaction conditions for coupling the water soluble polymer, preferably a poly(alkylene oxide), to the cyanovirin-N protein variant of the invention will vary depending upon the particular polymer moiety employed, the site of attachment on the cyanovirin-N protein variant, the particular type of reactive group (i.e., lysine versus cysteine), the desired degree of PEGylation, and the like, and can readily be determined by one skilled in the art.

Reactive groups suitable for activating a PEG-polymer for attachment to a thiol (sulfhydryl) group on a cyanovirin-N protein variant of the invention, as discussed above, include thiol, vinylsulfones, iodoacetamide, maleimide, and dithio-orthopyridine. Particularly preferred reagents include PEG-vinylsulfone and PEG-maleimide. Additional representative vinylsulfones for use in the present invention are described in U.S. Pat. No. 5,739,208, the content of which is expressly incorporated herein by reference.

In preferred embodiments, the compositions of the invention comprise selectively PEGylated cyanovirin-N protein variants, i.e., the conjugates are essentially homogeneous with respect to the position and degree of PEGylation. That is to say, site selective or site directed PEGylation of a cysteine group will result in a protein-polymer conjugate composition wherein PEG moieties are attached primarily at the intended target position(s) of the cyanovirin-N protein variant. Depending upon the intended site of PEGylation, a protection/deprotection synthetic strategy may be necessary to prevent PEGylation of non-target reactive sites within the cyanovirin-N protein variant. Such site-directed coupling chemistry results in conjugates having a large degree of substitution at a particular reactive site on the cyanovirin-N protein variant, e.g., at the C-terminal end, the N-terminal end, or a specific residue location of interest, as described above with regard to the preferred point mutations of the cyanovirin-N protein variants of the invention. Preferably, the conjugate composition includes one species of polymer-protein conjugate.

These compositions can then, if desired, be further purified to provide compositions of essentially pure protein-polymer conjugate. An essentially pure protein-polymer conjugate composition refers to a composition comprising a protein-polymer conjugate that is at least about 90% pure, and preferably at least about 95% pure; i.e. the composition contains at least about 90% by weight of protein-polymer conjugate species, while the remainder represents unconjugated protein, unconjugated polymer, dimeric side products, etc. Protein-polymer conjugates of the invention are typically purified using one or more purification techniques such as ion exchange chromatography, size exclusion chromatography, affinity chromatography, hydrophobic interaction chromatography, and reverse phase chromatography. For example, gel filtration can be used to separate PEGylated from unPEGylated protein, and anion exchange to remove unreacted PEG from the PEGylated protein.

The overall homogeneity of the resulting protein-polymer conjugates (i.e. the number of distinct protein-polymer species present, including positional isomers) can be assessed using one or more of the following methods: chromatography, electrophoresis, mass spectrometry, and in particular, MALDI-MS, and NMR spectroscopy.

The preparation of illustrative polymer conjugates in accordance with the invention is described in Examples 4 and 5. Example 4 describes the preparation of an exemplary conjugate in which a 20 kilodalton linear PEG, mPEG-orthopyridyl-disulfide, is site selectively coupled to cysteine in a mutant version of CV-N in which glutamine 62 is replaced by a cysteine. The resulting conjugate composition contains only one PEG-CV-N species, i.e., a monoPEGylated CV-N having polyethylene glycol specifically attached to position 62 in the CV-N protein. Example 5 similarly describes the preparation of an exemplary CV-N conjugate prepared by coupling a mutant version of CV-N in which glutamine 62 is replaced by a cysteine to a 30 kilodalton mPEG-maleimide. The resulting conjugate composition contains only one PEG-CV-N species where PEG has been site selectively attached to the 62-cysteine position of the CV-N variant.

D. Bioactivity

The bioactivity of two conjugates of the invention, designated $PEG_{30\ kDa}$-CV-N(Q62C) and $PEG_{20\ kDa}$-CV-N (Q62C), was evaluated in vitro against influenza virus (Example 7) and HIV (Example 8) according to known methods, and significant bioactivity was demonstrated. In the former case, the $ED_{50}$ of the conjugate was similar to that of native protein. Immunogenicity and acute toxicity testing in vivo (Examples 9-10) showed the conjugate $PEG_{30\ kD}$-CV-N(Q62C) to be significantly less immunogenic and less toxic than the native protein.

These results are in contrast to those obtained from a random PEGylation of the lysine residues and/or N-terminus of the native protein (see Comparative Example 1 below). This approach resulted in either very low yields and/or conjugates having insignificant levels of bioactivity, based upon an XTT-based cytoprotection assay.

V. Pharmaceutical Compositions

In yet another aspect of the invention, the variant cyanovirin-N—polymer conjugates of the invention may be formulated as pharmaceutical compositions useful for the treatment, prevention or mitigation of infection by high-mannose enveloped viruses. In this regard, "high mannose" refers to at least six, typically six to nine, linked mannose rings. High mannose envelope viruses which are currently known include human immunodeficiency virus, influenza virus, measles virus, herpes virus 6, marburg virus, and ebola virus.

Also provided are methods for the treatment, prevention or mitigation of infection by such viruses, comprising administering a therapeutically or prophylactically effective amount of a pharmaceutical composition of the invention.

The pharmaceutical compositions of the invention may be administered neat or formulated with additional excipients, solvents, stabilizers, adjuvants, diluents, etc., depending upon the particular mode of administration and dosage form. The present protein variants and/or conjugates may be administered parenterally as well as non-parenterally. Specific administration routes include oral, ocular, vaginal, rectal, buccal, topical, nasal, ophthalmic, subcutaneous, intramuscular, intraveneous, intracerebral, transdermal, and pulmonary.

Pharmaceutical compositions of the invention generally comprise a therapeutically or prophylactically effective amount of at least one protein-polymer conjugate of the invention together with one or more pharmaceutically acceptable carriers. Formulations of the present invention, e.g., for parenteral administration, are most typically liquid solutions or suspensions. Generally, the pharmaceutical compositions for parenteral administration will be formulated in a non-toxic, inert, pharmaceutically acceptable aqueous carrier medium, preferably at a pH of about 5 to 8, more preferably 6 to 8. Inhalable formulations for pulmonary administration are generally liquids or powders, with powder formulations being generally preferred. Pharmaceutical compositions of the invention can also be formulated as a lyophilized solid which is reconstituted with a physiologically appropriate solvent prior to administration. Additional albeit less preferred compositions of the proteins and/or protein-polymer conjugates of the invention include syrups, creams, ointments, tablets, and the like.

The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Pharmaceutically acceptable carriers are determined in part by the particular composition being administered, as well as by the particular method used to administer the composition. Accordingly, there is a wide variety of suitable formulations of pharmaceutical compositions of the present invention (see, e.g., Remington's Pharmaceutical Sciences, 17th ed. 1985).

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, pharmaceutical compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

The term "therapeutically or prophylactically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms, such as decreased body temperature. The precise effective amount for a subject will depend upon the subject's size and health, the nature and extent of the condition, and the therapeutics or combination of therapeutics selected for administration. Thus, it is not useful to specify an exact effective amount in advance. However, the effective amount for a given situation can be determined by routine experimentation and is within the judgement of the clinician.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example, a cyanovirin-N protein variant and/or protein-polymer conjugate of the invention, which ameliorates the symptoms or condition, or provides protection against infection. Therapeutic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $ED_{50}/LD_{50}$. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration.

The exact dosage will be determined by the practitioner, in light of factors related to the subject or patient requiring treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation. The clearance rate (i.e. the half-life) of the protein-polymer conjugate can be varied to fit the particular need of the patient by changing, for example, the number and/or size of PEG moieties on the protein.

Because the pharmacological profile of the protein is improved by conjugation, e.g. by reducing clearance rate, the dosage regimen of protein-polymer conjugate is generally equal to or less than an equivalent dosage, on a molecular basis, of the unconjugated protein. Normal dosage amounts may vary from 0.1 to 100 μg, up to a total dose of about 1 g, depending upon the route of administration. Guidance as to particular dosages and methods of delivery is provided in the literature and generally available to practitioners in the art.

The PEGylated proteins of the invention are preferably administered parenterally, e.g. by intramuscular or intravenous injection, thus avoiding the GI tract. Other modes of administration include transdermal and transmucosal administrations provided by patches and/or topical cream compositions. Transmucosal administrations can also include nasal spray formulations which include the PEGylated proteins of the invention within a nasal formulation which contacts the nasal membranes and diffuses through those membranes directly into the cardiovascular system. Aerosol formulations for intrapulmonary delivery can also be used.

The cyanovirin-N protein variants and protein-polymer conjugates of the invention can also be included in devices for fixation or delivery of the variant or conjugate to a site of interest. Such devices can include particles, magnetic beads, flow-through matrices, condoms, diaphragms, cervical caps, vaginal rings, sponges, foams, and gels. More particularly, the protein variants or protein-polymer conjugates of the invention can be covalently attached to the surface of a device via hydrolytically stable or unstable linkages. Alternatively, the protein variants or protein-polymer conjugates can be incorporated into the mechanical device, such as through the formation of foams and gels which utilize the protein variant or protein-polymer conjugate as an integral part of its core structure. Such devices can then be used in their ordinary manner to fix the variants and/or conjugates to a specific location or to deliver the variants and/or conjugates of the invention to a desired location.

One skilled in the art may refer to general reference texts for detailed descriptions of known techniques discussed herein or equivalent techniques. These texts include *Poly (ethylene glycol) Chemistry: Biotechnical and Biomedical Applications*, Harris (ed.), Plenum Press, New York (1992); Wong, *Chemistry of Protein Conjugation and Cross-Linking*, CRC Press (1991); Ausubel et al., *Current Protocols in Molecular Biology*, John Wiley and Sons, Inc. (1995); Sambrook et al., *Molecular Cloning, A Laboratory Manual* (2d ed.), Cold Spring Harbor Press, Cold Spring Harbor, N.Y. (1989); Birren et al., *Genome Analysis: A Laboratory Manual*, volumes 1 through 4, Cold Spring Harbor Press, Cold Spring Harbor, N.Y. (1997-1999); *Plant Molecular Biology: A Laboratory Manual*, Clark (ed.), Springer, N.Y. (1997); Richards et al., *Plant Breeding Systems* (2d ed.), Chapman & Hall, The University Press, Cambridge (1997); and Maliga et al, *Methods in Plant Molecular Biology*, Cold Spring Harbor Press, Cold Spring Harbor, N.Y. (1995).

EXAMPLES

The following examples illustrate but are not intended in any way to limit the invention.

Comparative Example 1

Non-Specific PEGylation of Cyanovirin-N

Cyanovirin-N was modified via non-specific PEGylation of the protein's amino groups. The PEG reagents employed were mPEG-succinimidyl propionic acid, 30 kD (SPA, Nektar Therapeutics, AL) or mPEG-propionaldehyde, 2 kD, 5 kD, or 30 kD (Nektar Therapeutics, AL). Non-specific attachment of the SPA reagent was carried out according to the methods set forth in U.S. Pat. No. 5,672,662. Modification of CV-N using the propionaldehyde reagent in the presence of a reducing agent was carried out according to convention methods (see, for example, Wirth, P. et al., 1991, *Bioorg. Chem.* 19:133).

The activity of the resultant PEG-modified CV-N samples was investigated using an XTT-based cytoprotection assay (CEM-SS cells/HIV-1$_{RF}$). All of the PEG-CV-N compositions were inactive or possessed extremely low activities when compared to native CV-N or mutant CV-N controls.

Example 2

Mutagenedid of Cyanovirin-N Coding Sequence

Positions gln14 and gln62 were selected as being particularly preferred for substitution with a cysteine residue, due to their distance from the reported active sites of native cyanovirin (Bewley, Calif., *Structure (Camb).*, 2001, 9(10): 931-40). The first site selected for substitution was gln62.

The gene encoding cyanovirin-N (CV-N) was obtained from the National Cancer Institute (see U.S. Patent Application Publication No. US 2002/0127675, which is incorporated herein by reference). The gene contained the coding sequence SEQ ID NO: 9 and had been cloned into the pET26(b) expression vector (Novagen, Madison, Wis.), which contains a pelB signal sequence that directs periplasmic translocation.

The mutagenesis was accomplished using the QuikChange mutagenesis kit (Stratagene, La Jolla, Calif.) according to the manufacturer's protocol. The PCR primers used in the reaction had the following sequences:

```
                                                  (SEQ ID NO: 10)
5'-CAACTCCGCTATCTGCGGTTCCGTTCTGACCTCC-3'

3'-GTTGAGGCGATAGACGCCAAGGCAAGACTGGAGG-5'
```

Two PCR reactions were set up, each containing 5 μl of 10× reaction buffer (100 mM KCl, 100 mM (NH$_4$)$_2$SO$_4$, 100 mM Tris-HCl, pH 8.8, 20 mM MgSO$_4$, 1% Triton X-100, and 1 mg/ml bovine serum albumin (BSA)), 1 μl of each of the above primers, 1 μl of dNTPs, 25 or 50 ng of native CV-N, 1 μl of Pfu DNA polymerase, and sterile, deionized water to a final volume of 50.0 μl. The reactions were incubated in a thermal cycler (Eppendorf, Mastercycler Personal) with the following reaction conditions: 1, 30 second cycle at 95° C., and 16 cycles of a 30 second 95° C.

step followed by one minute at 55° C., and 11 minutes 20 seconds at 68° C. Following this process, the remaining unmodified DNA was digested with 1 µl of DpnI endonuclease by placing the reactions at 37° C. for 1 hour. The plasmid DNA was transformed into XL1-Blue *Escherichia coli*, and plated on Luria Broth-agar medium containing 30 µg/ml kanamycin, and then placed at 37° C. overnight.

To determine whether or not the Q62C mutation had been incorporated into the CV-N coding sequence, individual colonies were selected and the plasmid DNA recovered using the Promega Wizard Miniprep purification kit according to the manufacturer's instructions (Promega, Madison, Wis.). The plasmid DNA was then sequenced by ResGen (Huntsville, Ala). Incorporation of the Q62C mutation (as shown in SEQ ID NO: 12) was confirmed.

Example 3

Expression and Purification of CV-N(Q62C)

CV-N(Q62C) DNA, prepared as described in Example 2, was transformed into BL21(DE3) *E. coli* (Novagen, Madison, Wis.). The mutant CV-N(Q62C) protein was expressed according to the method of Mori (Mori et al., *Prot Expr and Purif.* 1998 Mar.;12(2): 151-8).

Briefly, a single colony of CV-N in BL21(DE3) *E. coli* grown on selective LB-agar plates containing kanamycin (30 μg/ml) was inoculated into Superbroth (32 g of tryptone, 20 g yeast extract, and 5 g NaCl per liter) containing 0.5% glucose, 1.6 mM sterile-filtered $MgSO_4$, and 30 μg/ml kanamycin and grown overnight at 37° C. at 225 rpm in a shaking incubator (New Brunswick Scientific, New Brunswick, N.J.). The following day, the overnight culture was added to 5 L of Superbroth of the same composition as described above, at a 1:50 dilution. The expression of CV-N(Q62C) was carried out in a 6 L fermentation vessel (BioFlo3000, New Brunswick Scientific, New Brunswick, N.J.) under the following conditions: agitation at 300 rpm, 30% dissolved oxygen, 37° C., pH 7.0. Growth of the cells was monitored via measurement of the optical density at 600 nm ($OD_{600}$). When the $OD_{600}$ reached approximately 1.2, expression of CV-N(Q62C) was induced using isopropylthiogalactosidase (IPTG) at a final concentration of 1.0 mM. The expression was allowed to continue for approximately two hours until the culture reached an $OD_{600}$ of about 1.6. The cells then were harvested by centrifugation at 7000×g for 10 minutes at 4° C.

The initial purification method used was based upon the method of Mori et al. (cited above), with several modifications. The first stage of purification was a periplasmic fractionation, to isolate only those proteins found in the periplasm. The recovered cell pellet was resuspended in a solution containing 30 mM Tris-HCl, pH 8.0, 20% sucrose (w/v), and 1 mM EDTA with a volume of 1/20 the original culture volume. The cells were shaken gently at 4° C. for 30 minutes. The cells were centrifuged at 4000×g at 4° C. for 15 minutes. The supernatant from this stage was labeled as the periplasmic fraction. The cell pellet was then resuspended in a 1/20 original culture volume of ice-cold 5 mM $MgSO_4$:1 mM EDTA and gently shaken at 4° C. for 30 minutes. This resuspension was then centrifuged at 15,000×g for 20 minutes at 4° C. The supernatant was labeled as the osmotic fraction and the pellet was discarded.

The fractions were subsequently analyzed via SDS-PAGE to determine which fraction contained the CV-N(Q62C). As the protein of interest was found primarily in the osmotic fraction, only this fraction was purified further.

Because the presence of the unpaired cysteine residue made the protein susceptible to dimerization, the protein solution was reduced with mercaptoethylamine (MEA, Sigma) prior to purification. The volume of protein solution was measured, and MEA was added to a final concentration of 50 mM. The solution was then placed in a 37° C. water bath for 90 minutes.

After reduction, the protein solution was concentrated via ultrafiltration using a stirred cell (Amicon Model 8200, Millipore, Bedford, Mass.) containing 3,000 MWCO polyethersulfone membrane (Millipore, Bedford, Mass.). The protein was concentrated to a final volume of approximately 20 ml under argon at 55 psi.

The protein was purified via gel filtration chromatography, using a Superdex 75 HiLoad 16/60 column (Amersham Biosciences North America, Piscataway, N.J.). This and all subsequent chromatographic separations were carried out on an AktaPrime chromatography system (Amersham Biosciences North America, Piscataway, N.J.). For each separation, 2 ml of concentrated protein solution was loaded onto the column. The separation was carried out using a pH 4.0, 10 mM citrate buffer (10 mM citric acid, 10 mM sodium citrate) at a flow rate of 1.5 ml/min. Three ml fractions were collected, beginning at a volume of 90 ml post-injection, and continuing until 120 ml post-injection. The fraction containing CV-N(Q62C) was identified using SDS-PAGE, and it was determined that the protein consistently eluted beginning at 100 ml post-injection.

The CV-N (Q62C) was also purified, in subsequent preparations, using an acid precipitation step followed by cation exchange chromatography.

A position 14 mutant, having a cysteine substituted at the gin 14 position of native cyanovirin (Q14C), was similarly expressed. The position 62 mutant described above was chosen for preparing the illustrative polymer conjugate described below, due to its superior level of expression in the expression systems utilized.

Example 4

Modification of CV-N(Q62C) with PEG-O-Pytidyl Disulfide

Following purification by gel filtration, the concentration of CV-N(Q62C) was determined using an enzyme-linked immunosorbant assay (ELISA). In order to generate a standard curve, native CV-N was added to one column of wells of a 96-well plate in serial dilutions (with phosphate buffered saline) resulting in concentrations ranging from 2 μg/ml to 0.01 μg/ml. CV-N(Q62C) was serially diluted from 1:5 to 1:640 with PBS, and 60 μl of each CV-N(Q62C) dilution was added to wells of the same plate. The plates were incubated overnight at room temperature (22-24° C.) in a humidified container. The following day, the plates were rinsed 3 times with deionized water and then blocked with 200 μl of blocking buffer for 30 minutes at room temperature. The plates were washed as above and then incubated for two hours with 60 μl of rabbit polyclonal anti-CV-N antibody (NCI) that had been diluted 1:3000 with blocking buffer from its initial concentration of 1 mg/ml. The plates were rinsed three times with deionized water, blocked with 200 μl of blocking buffer at room temperature for 10 minutes, and then rinsed an additional 3 times. 60 μl of a 1:3000 dilution of goat anti-rabbit IgG-horseradish peroxidase conjugate (GAR-HRP) was added to each well containing CV-N(Q62C). The plates were incubated at room temperature for 1.5 hours, then rinsed and blocked as previously described.

For color development, 75 μl of an equal mixture of 3,3',5,5'-tetramethylbenzidine (0.4 mg/ml) and $H_2O_2$ (0.02% in citric acid buffer) (Kirkegaard and Perry Laboratories, Gaithersburg, Md.) was added to each well, and once the color reached an appropriate intensity, the reaction was quenched by adding 25 μl of 1 M $H_2SO_4$ to each well. The absorbance at 450 nm was measured, and a standard curve was generated by plotting the logarithm of the native CV-N concentration in each well against the absorption measured for the same wells. The concentration of the CV-N(Q62C) was determined from this graph.

SITE SPECIFIC PEGYLATION: The CV-N(Q62C) was modified using the exemplary sulfhydryl-specific polymer, 20 kDa methoxy-PEG-orthopyridyl-disulfide ($mPEG_{20\ kDa}$-OPSS, Shearwater Corp., Huntsville, Ala.). For a description of the reaction see e.g. C. Woghiren et al, *Bioconj. Chem.* 4:314 (1993). A five-fold molar excess of $m\text{-}PEG_{20\ kDa}$-OPSS was added to the purified CV-N(Q62C) to form the resulting CV-N(Q62C)-PEG conjugate. The reaction was conducted overnight at room temperature.

ANALYSIS: Modification of the CV-N(Q62C) was established via SDS-PAGE and matrix-assisted laser desorption ionization-time of flight (MALDI-TOF) mass spectrophotometer (Hewlett-Packard). The data confirmed formation of a PEGylated cyanovirin species, where the PEG chain was covalently attached in a site selective manner to the 62-cysteine residue of the cyanovirin mutant described above.

PURIFICATION OF THE CV-N-(Q62C) PEG CONJUGATE: CV-N (Q62C) modified with $mPEG_{20\ KD}$a-OPSS (hereafter referred to as PEG-CV-N(Q62C)) was isolated from unreacted CV-N(Q62C) by first concentrating the solution using ultrafiltration as described above, followed by gel filtration using the same conditions outlined above.

Because the unreacted $mPEG_{20\ KDa}$-OPSS eluted from the gel filtration column in the same volume as the PEG-CV-N(Q62C), an additional purification step was required to separate the two species. The PEG-CV-N(Q62C) was separated from the unreacted PEG reagent using a 20 ml CM Sepharose cation exchange column (Amersham Biosciences North America, Piscataway, N.J.). The column was equilibrated with 5 column volumes of 10 mM citrate buffer (buffer A) prior to loading 5 ml of concentrated PEG-CV-N(Q62C). The column was then washed with another 5 column volumes of buffer A. The PEG-CV-N(Q62C) was isolated from unreacted $mPEG_{20\ KDa}$-OPSS using a step gradient. The first step had a length of 2 column volumes at 60% 10 mM citrate buffer, 0.25 M NaCl, pH 4.0 (Buffer B). The second step was 3 column volumes in duration at 100% of Buffer B. Finally, the column was reequilibrated with 2 column volumes of 10 mM citrate, 1 M NaCl, pH 4.0. The method ended with a 2 column volume was with Buffer A.

The purity of the sample was determined using SDS-PAGE and MALDI-TOF.

Example 5

Modification of CV-N(Q62C) with $MPEG3_{30\ kD}$-Maleimide

CV-N(Q62C) was purified using an acid precipitation step followed by cation exchange chromatography. The pH of the purified protein solution was adjusted to neutral, and site specific PEGylation at position Q62C was performed using a two-fold molar excess of $mPEG_{30\ kD}$-maleimide (Nektar AL, Huntsville, Ala.). (See e.g. U.S. Pat. No. 6,602,498.) The $PEG_{30\ kD}$-MAL-CV-N(Q62C) conjugate was separated from unreacted PEG-MAL and unmodified CV-N using anion exchange chromatography followed by gel filtration.

Protein purity and reaction yield were monitored by reverse phase HPLC. Protein concentrations were determined using the BCA protein assay. The reaction yield was approximately 70% following purification.

As demonstrated below, site-selective cysteine mutants of CV-N retained significant activity when conjugated to different molecular weight sulfhiydryl-reactive PEGs (Examples 6-8). The conjugates also showed significantly reduced toxicity and immunogenicity relative to unmodified CV-N (Examples 9-10).

Example 6

Determination of Bioactivity of $PEG_{20\ KDA}$-CV-N(Q62C)

Using an Influenza Virus Inactivetion Assay

Volumes of 100 μl well of Maiden-Darby Canine Kidney (MDCK) cells ($4 \times 10^5$ cells/ml) in Dulbecco's Modified Eagles Medium (DMEM) containing 10% fetal calf serum and 100 units/ml penicillin, 100 μg/ml streptomycin, and 0.25 μ/ml amphotercin were seeded into wells of 96-well plates. The following day, serial dilutions ($10^{-2}$-$10^{-8}$) of test sample (CV-N, CV-N mutant, PEG 20 kDa CV-N mutant, or PEG 20 kDa OPSS) were prepared using DMEM without serum in a final volume of 100 μl. Two hundred times the 50% tissue culture infectious dose ($TCID_{50}$) of influenza A/Udorn (H3N2) (NIH) in a 100 μl volume of DMEM was then added to the test sample dilutions, and the mixture was incubated for 1 hour at room temperature. The test sample/influenza solution was supplemented with an N-tosyl-L-phenylalanyl chloromethyl ketone (TPCK)-trypsin solution (Sigma-Aldrich, St. Louis, Mo.), at a final concentration of 1.25 μg/ml. 100 μl of this resulting solution was then added to the MDCK cells that had been previously washed with phosphate buffered saline (PBS).

As controls, MDCK cells were also treated with the following components: medium only, virus only, and a $10^{-2}$ dilution of test sample.

On day 5, wells were examined using a microscope (Nikon TS100), and the highest dilution at which 50% of the cells were still protected from infection was calculated. Data is presented as the dose required to protect 50% of MDCK cells from influenza infection ($ED_{50}$).

| Sample | $ED_{50}$ |
|---|---|
| CV-N standard (NIH, 1 mg/ml) | 2.56 nM |
| CV-N(Q62C) | 0.45 nM |
| $PEG_{20\ kDa}$-CV-N(Q62C) | 2.27 nM |
| $PEG_{20\ kDa}$-OPSS (reagent) | $1 \times 10^4$ nM |

Example 7

Bioactivity of $PEG2_{20\ KDA}$-CV-N(Q62C) Against HIV

Bioassays were conducted at the National Cancer Institute using the methods described in U.S. Pat. No. 5,843,883 (column 20, lines 20-55), which patent is incorporated herein by reference. The $PEG_{20}$ kDa -CV-N (Q62C) conjugate exhibited an $ED_{50}$ of 46 ng/mL, while the $ED_{50}$ of native CVN was 1 ng/mL.

Example 8

Anti-Bioactivity of CV-N MUTANT PEG Conjugates

The anti-HIV activity of the modified native and mutant proteins as well as the PEG conjugates described above was evaluated using an in vitro XTT-based cryoprotection assay using CEM-SS cells and the HIV-1 RF strain.

Figure 2:
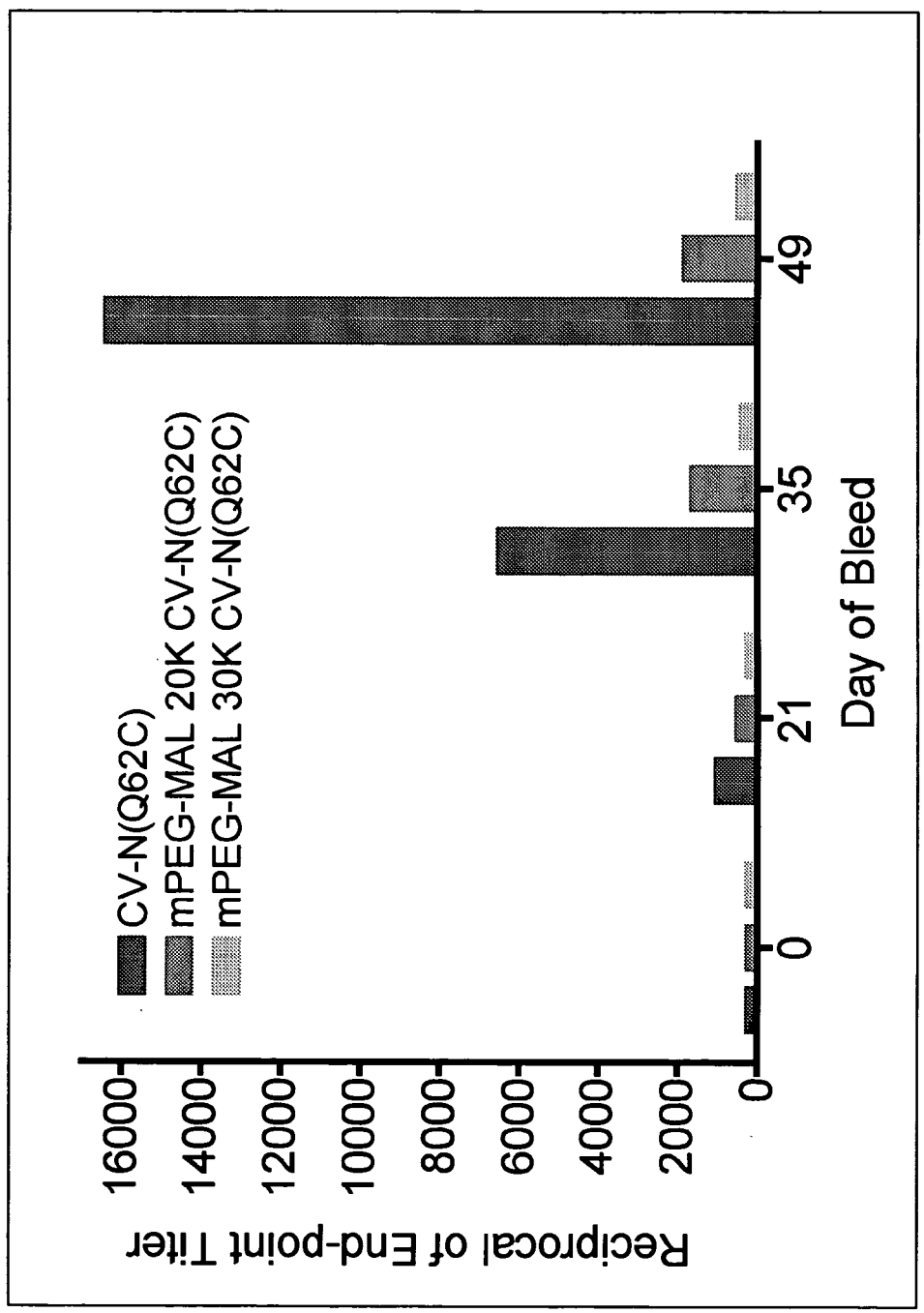
FIG. 2 is a bar graph demonstrating the relative immunogenicity of PEGylated and non-PEGylated CV-N positional mutants of the invention.

The anti-HIV activity of the exemplary PEGylated CV-N mutants of the invention is provided in FIG. 2. Activity is expressed as the concentration at which the test compound protects 50% of the CEM-SS cells from infection from the RF strain of HIV ($IC_{50}$). The $IC_{50}$ is depicted in FIG. 2 relative to AZT, with the AZT activity assigned a value of 1.0. Because the cell-based assay showed significant variability from one assay to the next, all sample $IC_{50}$ values were normalized against AZT for each run.

Although the 30 K PEG CV-N mutant (i.e. $PEG_{30\ kD}$-MAL-CV-N(Q62C) ) showed less activity than the other illustrative conjugate (i.e. $PEG_{20\ kDa}$ OPSS-CV-N (Q62C)), the former compound was selected for further testing due to advantages conferred in vivo by utilizing a larger PEG molecule.

Example 9

Acute Toxicity Study of CV-N MUTANT PEG Conjugates

To compare the acute toxicity of native CV-N and the $PEG_{30\ kD}$-MAL-CV-N(Q62C) conjugate, an in vivo dose escalation study was performed in which Hsd:ICR(CD-1) mice were administered modified or unmodified CN-N intravenously on three consecutive days.

Administration of high doses of native CV-N resulted in the death of all of the mice in that particular group. However, the mice given an equivalent does of the $PEG_{30\ kD}$-CV-N mutant compound exhibited only a minor photosensitivity reaction and were still healthy when sacrificed at the end of the observation period.

Example 10

Immunogenicy of CV-N Mutant PEG Conjugates

Unmodified CV-N(Q62C) elicited a large immune response in mice, having a 50% endpoint titer of 16384 (FIG. 3). In comparison, CV-N(Q62C)-MAL 20K had a 50% endpoint titer of 1825, and CV-N(Q62C)-MAL 30K had an endpoint titer of only 512, merely twice that of the baseline reading.

It is claimed:

1. An antiviral polypeptide having at least 70% sequence identity to native cyanovirin-N (SEQ ID NO. 1) and having fewer than five non-conservative amino acid substitutions relative to native cyanovirin-N (SEQ ID NO. 1), wherein said polypeptide is modified relative to SEQ ID NO: 1to contain 1-4 reactive sites for selective conjugation, each said reactive site being selected from:

(a) a cysteine substitution or insertion at at least one position selected from the group consisting of 5, 9-21, 25, 29-40, 45-49, 52, 57, 59-72, 79-91, 96-101 of SEQ ID NO: 1, the C-terminus, and the N-terminus; and (b) a single lysine residue remaining after arginine substitution of all but one of the lysine residues in the polypeptide;

or a fragment thereof, wherein the fragment includes the sequence set forth in residue 40-80 of SEQ ID NO: 1, modified to contain at least one said reactive site for selective conjugation.

2. The antiviral polypeptide of claim 1, wherein said antiviral polypeptide has a cysteine substitution or insertion at at least one position selected from the group consisting of 5, 9-21, 25, 29-40, 45-49, 52, 57, 59-72, 79-91, 96-101, the C-terminus, and the N-terminus; or an arginine substitution at at least four residues selected from the group consisting of 3, 48, 74, 84, and 99; and otherwise has the sequence set forth in SEQ ID NO: 1.

3. The polypeptide of claim 2, having one to four cysteine substitutions or insertions at positions selected from the group consisting of 5, 9-21, 25, 29-40, 45-49, 52, 57, 59-72, 79-91, 96-101, the C-terminus, and the N-terminus.

4. The polypeptide of claim 3, wherein said positions are selected from the group consisting of 9-21, 29-40, 45-49, 57, 59-72, 79-91, and 96-101.

5. The polypeptide of claim 4, wherein said positions are selected from the group consisting of 10-20, 31-39, 46-48, 60-71, 80-90, and 97-100.

6. The polypeptide of claim 4, wherein said positions are selected from the group consisting of 11, 14, 16, 19, 20, 31, 32, 33, 38, 46, 61, 62, 67, 68, 82, and 83.

7. The polypeptide of claim 3, having one or two cysteine substitutions or insertions.

8. The polypeptide of claim 7, having a single cysteine substitution, at position 62 or position 14.

9. The polypeptide of claim 8, having a cysteine substitution at position 62.

10. The polypeptide of claim 2, having arginine substitutions at at least four residues selected from the group consisting of 3, 48, 74, 84, and 99.

11. An fragment of antiviral polypeptide of claim 2, comprising at least twenty contiguous amino acids and spanning at least one of the substitutions or insertions of the antiviral polypeptide of claim 2.

12. The fragment of claim 11, comprising at least forty contiguous amino acids and spanning at least one of the substitutions or insertions of the antiviral polypeptide of claim 2.

13. The fragment of claim 12, wherein said fragment includes a region spanning at least one of the substitutions or insertions of the antiviral polypeptide of claim 2 and otherwise having the sequence set forth in residues 41-78 of native cyanovirin-N (SEQ ID NO: 1).

14. The fragment of claim 13, having a cysteine substitution at position 62.

15. A polynucleotide encoding an antiviral polypeptide as recited in claim 1.

16. The polynucleotide of claim 15, encoding an antiviral polypeptide as recited in claim 2.

17. The polynucleotide of claim 15, encoding an antiviral polypeptide as recited in claim 8.

18. A vector comprising a polynucleotide as recited in claim 15.

19. A host cell comprising a vector as recited in claim 18.

20. An antiviral polypeptide-polymer conjugate, comprising
   (i) an antiviral polypeptide having at least 70% sequence identity to native cyanovirin-N (SEQ ID NO. 1), and having fewer than five non-conservative amino acid substitutions relative to native cyanovirin-N (SEQ ID NO. 1), wherein said polypeptide is modified relative to SEQ ID NO: 1 to contain 1-4 reactive sites for selective conjugation, each said reactive site being selected from:
   (a) a cysteine substitution or insertion at at least one position selected from the group consisting of 5, 9-21, 25, 29-40, 45-49, 52, 57, 59-72, 79-91, 96-101 of SEQ ID NO: 1, the C-terminus, and the N-terminus, and
   (b) a single lysine residue remaining after arginine substitution of all but one of the lysine residues in the polypeptide;
   or a fragment thereof, wherein the fragment includes the sequence set forth in residues 40-80 of SEQ ID NO: 1, modified to contain at least one said reactive site for selective conjugation; and
   (ii) a water soluble polymer covalently attached to the polypeptide or fragment thereof at at least one of said reactive sites.

21. The conjugate of claim 20, wherein said antiviral polypeptide has a cysteine substitution or insertion at at least one position selected from the group consisting of 5, 9-21, 25, 29-40, 45-49, 52, 57, 59-72, 79-91, 96-101, the C-terminus, and the N-terminus; or an arginine substitution at at least four residues selected from the group consisting of 3, 48, 74, 84, and 99; and otherwise has the sequence set forth in SEQ ID NO. 1.

22. The conjugate of claim 21, wherein the water-soluble polymer is attached at a site of cysteine substitution at a position selected from the group consisting of 5, 9-21, 25, 29-40, 45-49, 52, 57, 59-72, 79-91, 96-101.

23. The conjugate of claim 21, wherein the water-soluble polymer is attached at a site of cysteine substitution at a position selected from the group consisting of 11, 14, 16, 19, 20, 31, 32, 33, 38, 46, 61, 62, 67, 68, 82, and 83.

24. The conjugate of claim 22, comprising one to four attached water-soluble polymers.

25. The conjugate of claim 23, comprising one or two attached water-soluble polymers.

26. The conjugate of claim 25, comprising a single attached water-soluble polymer at a cysteine substitution at position 14 or position 62.

27. The conjugate of claim 21, wherein the polymer is a polyalkylene oxide.

28. The conjugate of claim 27, wherein the polymer is a polyethylene glycol (PEG).

29. The conjugate of claim 28, wherein the polymer is attached to a cysteine residue substituted at position 62 of an antiviral polypeptide which other has the sequence set forth in SEQ ID NO. 1.

30. The conjugate of claim 29, wherein the polymer has an average molecular weight in the range of about 350 daltons to about 100,000 daltons.

31. The conjugate of claim 30, wherein the polymer has an average molecular weight in the range of about 5,000 daltons to about 40,000 daltons.

32. The conjugate of claim 31, wherein said polymer has an average molecular weight in the range of about 20,000 to 40,000 Daltons.

33. The conjugate of claim 20, wherein the antiviral polypeptide or fragment is covalently attached to the water soluble polymer via a linkage selected from the group consisting of: amide, secondary amine, ester, disulfide, ether, thioether, urea, and carbamate.

34. The conjugate of claim 28, wherein said polyethylene glycol comprises one or more degradable linkages.

35. A pharmaceutical composition comprising a therapeutically or prophylactically effective amount of a polymer conjugate as recited in claim 20 and a pharmaceutically acceptable carrier.

36. The pharmaceutical composition of claim 35, comprising a polymer conjugate as recited in claim 21.

37. The pharmaceutical composition of claim 36, comprising a polymer conjugate as recited in claim 23.

38. The pharmaceutical composition of claim 36, comprising a polymer conjugate as recited in claim 29.

39. A method for the treatment or mitigation of infection by at least one high mannose envelope virus, by administering to a patient in need of such treatment a pharmaceutically effective amount of a pharmaceutical composition as recited in claim 35.

40. The method of claim 39, wherein said envelope virus is selected from the group consisting of immunodeficiency virus, influenza virus, measles virus, herpes virus 6, marburg virus, and ebola virus.

41. The method of claim 40, comprising administering a pharmaceutical composition which comprises a pharmaceutically acceptable carrier and a therapeutically effective amount of an antiviral polypeptide-polymer conjugate, wherein the polymer is a polyethylene glycol (PEG) and is attached to a cysteine residue substituted at position 62 of an antiviral polypeptide which otherwise has the sequence set forth in SEQ ID NO. 1.

42. A composition comprising no more than one species of polymer conjugate as recited in claim 20.

43. The composition of claim 42, comprising no more than one species of polymer conjugate as recited in claim 21.

44. The composition of claim 43, comprising no more than one species of polymer conjugate as recited in claim 23.

45. The conjugate of claim 20, wherein said polypeptide has at least 80% sequence identity to native cyanovirin-N (SEQ ID NO. 1).

* * * * *